(12) United States Patent
Tal et al.

(10) Patent No.: US 11,344,314 B2
(45) Date of Patent: May 31, 2022

(54) CATHETERS WITH SIDE OPENINGS FOR MODIFYING AND DELIVERING SUSPENSIONS TO A SUBJECT

(71) Applicant: ACCURATE MEDICAL THERAPEUTICS LTD., Tel-Aviv (IL)

(72) Inventors: Michael Gabriel Tal, Savyon (IL); Eran Miller, Moshav Beit Elazari (IL)

(73) Assignee: ACCURATE MEDICAL THERAPEUTICS LTD., Tel-Aviv (IL)

( * ) Notice: Subject to any disclaimer, the term of this patent is extended or adjusted under 35 U.S.C. 154(b) by 560 days.

(21) Appl. No.: 15/554,825

(22) PCT Filed: Mar. 2, 2016

(86) PCT No.: PCT/IB2016/051175
§ 371 (c)(1),
(2) Date: Aug. 31, 2017

(87) PCT Pub. No.: WO2016/139597
PCT Pub. Date: Sep. 9, 2016

(65) Prior Publication Data
US 2018/0049747 A1   Feb. 22, 2018

Related U.S. Application Data

(60) Provisional application No. 62/127,036, filed on Mar. 2, 2015.

(51) Int. Cl.
*A61B 17/12*   (2006.01)
*A61M 25/00*   (2006.01)
(Continued)

(52) U.S. Cl.
CPC .. *A61B 17/12181* (2013.01); *A61B 17/12109* (2013.01); *A61B 17/12186* (2013.01);
(Continued)

(58) Field of Classification Search
CPC ............ A61M 25/007; A61M 25/0015; A61M 25/0068; A61M 2025/006;
(Continued)

(56) References Cited

U.S. PATENT DOCUMENTS 3,888,249 A * 6/1975 Spencer ............ A61M 25/0021
604/247
5,178,611 A   12/1993 Rosenberg
(Continued)

FOREIGN PATENT DOCUMENTS

CA      2382871      3/2001
CN    102665608      9/2012
(Continued)

OTHER PUBLICATIONS

International Search Report of PCT/IB2016/051175 Completed: Sep. 5, 2016; dated Sep. 15, 2016 9 pages.
(Continued)

*Primary Examiner* — Kevin C Sirmons
*Assistant Examiner* — Alexandra Lalonde
(74) *Attorney, Agent, or Firm* — The Roy Gross Law Firm, LLC; Roy Gross

(57) ABSTRACT

Microcatheters and methods for modifying and delivering suspended particles to target bodily parts (e.g., of a cardiovascular system). Embolization microcatheters and uses thereof in performing local embolization procedures, involving modifying flow characteristics (momentum) of suspensions during delivery. Applicable for delivering embolization material in a small blood vessel towards a target bodily part, and for performing local embolizations in small blood vessels feeding (possibly, cancerous) target bodily parts, thereby forming emboli therein, while preventing or minimizing non-target embolization. An exemplary catheter includes: a tubular wall with proximal and distal wall ends,
(Continued)

and a lumen extending therebetween, opened and configured to allow passage of a suspension to a distal outlet; the distal outlet shaped or/and sized to allow passage of both a suspension fluid and particles; a proximal outlet configured to allow passage of the suspension fluid without particles and to block passage of the particles, during delivery of the suspension.

10 Claims, 13 Drawing Sheets

(51) Int. Cl.

| | |
|---|---|
| *A61K 9/00* | (2006.01) |
| *A61K 9/16* | (2006.01) |
| *A61K 31/704* | (2006.01) |
| *A61L 24/00* | (2006.01) |
| *A61L 24/02* | (2006.01) |
| *A61F 2/01* | (2006.01) |
| *A61M 5/00* | (2006.01) |

(52) U.S. Cl.

CPC .......... *A61K 9/0019* (2013.01); *A61K 9/1676* (2013.01); *A61K 31/704* (2013.01); *A61L 24/0015* (2013.01); *A61L 24/02* (2013.01); *A61M 25/0074* (2013.01); *A61B 2017/1205* (2013.01); *A61F 2/011* (2020.05); *A61F 2002/016* (2013.01); *A61L 2300/23* (2013.01); *A61L 2300/416* (2013.01); *A61L 2430/36* (2013.01); *A61M 5/007* (2013.01); *A61M 25/007* (2013.01); *A61M 25/0021* (2013.01); *A61M 2025/0042* (2013.01)

(58) Field of Classification Search

CPC ...... A61M 2025/0073; A61M 2206/20; A61M 25/0009; A61M 25/0067; A61M 25/0043; A61M 25/0075; A61M 25/0074; A61M 25/0021; A61M 25/0023; A61M 25/0026; A61M 25/0028; A61M 25/0029; A61M 25/003; A61M 25/0054; A61M 2025/0042; A61M 2206/10; A61B 17/12109; A61B 17/12186; A61B 17/12099; A61B 17/12022; A61B 17/12; A61B 17/12181; A61B 17/12131; A61B 17/1205

See application file for complete search history.

(56) References Cited

U.S. PATENT DOCUMENTS

| | | | | |
|---|---|---|---|---|
| 5,318,032 | A | 6/1994 | Lonsbury et al. | |
| 5,573,520 | A | 11/1996 | Schwartz et al. | |
| 5,601,539 | A | 2/1997 | Corso, Jr. | |
| 5,749,894 | A | 5/1998 | Engleson | |
| 5,817,057 | A | 10/1998 | Berenstein et al. | |
| 5,833,671 | A | 11/1998 | Macoviak et al. | |
| 5,964,223 | A | 10/1999 | Baran | |
| 6,146,373 | A | 11/2000 | Cragg et al. | |
| 6,280,434 | B1 * | 8/2001 | Kinoshita ......... | A61M 25/0041 600/435 |
| 6,695,809 | B1 | 2/2004 | Lee | |
| 8,846,099 | B2 | 9/2014 | Nadal Ginard | |
| 9,468,739 | B2 | 10/2016 | Sutherland et al. | |
| 2001/0036451 | A1 | 11/2001 | Goupil et al. | |
| 2002/0143348 | A1 | 10/2002 | Wallace et al. | |
| 2002/0197246 | A1 | 12/2002 | Toombs | |
| 2003/0045842 | A1 * | 3/2003 | Kawakita ............ | A61M 25/007 604/264 |
| 2003/0130682 | A1 | 7/2003 | Broome et al. | |
| 2004/0006306 | A1 | 1/2004 | Evans et al. | |
| 2004/0122362 | A1 | 6/2004 | Houser et al. | |
| 2004/0176743 | A1 | 9/2004 | Morris et al. | |
| 2006/0004316 | A1 | 1/2006 | Difiore et al. | |
| 2007/0073271 | A1 * | 3/2007 | Brucker ............ | A61M 25/0043 604/537 |
| 2007/0135791 | A1 | 6/2007 | Slater et al. | |
| 2007/0225634 | A1 | 9/2007 | Ferren et al. | |
| 2008/0039786 | A1 | 2/2008 | Epstein et al. | |
| 2008/0188831 | A1 | 8/2008 | Bonnette et al. | |
| 2008/0188928 | A1 * | 8/2008 | Salahieh ........... | A61M 25/0054 623/2.11 |
| 2011/0082427 | A1 | 4/2011 | Golzarian et al. | |
| 2011/0152741 | A1 | 6/2011 | Banchieri et al. | |
| 2011/0182998 | A1 | 7/2011 | Reb et al. | |
| 2011/0245766 | A1 | 10/2011 | Leonard et al. | |
| 2011/0251629 | A1 | 10/2011 | Galdonik et al. | |
| 2012/0041419 | A1 | 2/2012 | Blanchard et al. | |
| 2012/0116351 | A1 | 5/2012 | Chomas et al. | |
| 2012/0245562 | A1 | 9/2012 | Bihlmaier | |
| 2013/0267845 | A1 * | 10/2013 | Howle .................. | A61M 5/007 600/432 |
| 2013/0338643 | A1 * | 12/2013 | De Silva ............... | B29C 66/723 604/533 |
| 2015/0088090 | A1 | 3/2015 | Macy, Jr. | |
| 2016/0074621 | A1 | 3/2016 | Yao et al. | |
| 2017/0368306 | A1 | 12/2017 | Tal et al. | |

FOREIGN PATENT DOCUMENTS

| | | | | |
|---|---|---|---|---|
| EP | 1857134 | | 11/2007 | |
| EP | 2010263 | | 1/2009 | |
| EP | 2777738 | | 9/2014 | |
| JP | H11276592 | | 10/1999 | |
| JP | H11-513293 | A | 11/1999 | |
| JP | 2008509781 | A | 3/2006 | |
| JP | 2007-511290 | A | 5/2007 | |
| JP | 2011178784 | A | 9/2011 | |
| JP | 2011529946 | A | 12/2011 | |
| JP | 2013-512735 | B2 | 4/2013 | |
| WO | 9721455 | | 6/1997 | |
| WO | 9833544 | | 8/1998 | |
| WO | 0132240 | | 5/2001 | |
| WO | 2004071495 | A1 | 8/2004 | |
| WO | 2005049110 | | 6/2005 | |
| WO | 2005049110 | A2 | 6/2005 | |
| WO | 2005058198 | | 6/2005 | |
| WO | 2007067255 | | 6/2007 | |
| WO | 2008067362 | | 6/2008 | |
| WO | 2009132065 | | 10/2009 | |
| WO | 2010026578 | | 3/2010 | |
| WO | 2010125159 | | 11/2010 | |
| WO | WO-2010125159 | A1 * | 11/2010 | ........ A61M 25/0084 |
| WO | 2011068924 | A1 | 6/2011 | |
| WO | 2011091275 | | 7/2011 | |
| WO | 2013126456 | A1 | 8/2013 | |
| WO | 2014047179 | | 3/2014 | |
| WO | WO-2015001456 | A1 * | 1/2015 | .......... A61M 25/007 |
| WO | 2015195646 | | 12/2015 | |

OTHER PUBLICATIONS

Written Opinion of the International Searching Authority of PCT/IB2016/051175 Completed: Sep. 5, 2016; dated Sep. 15, 2016 13 pages.

* cited by examiner

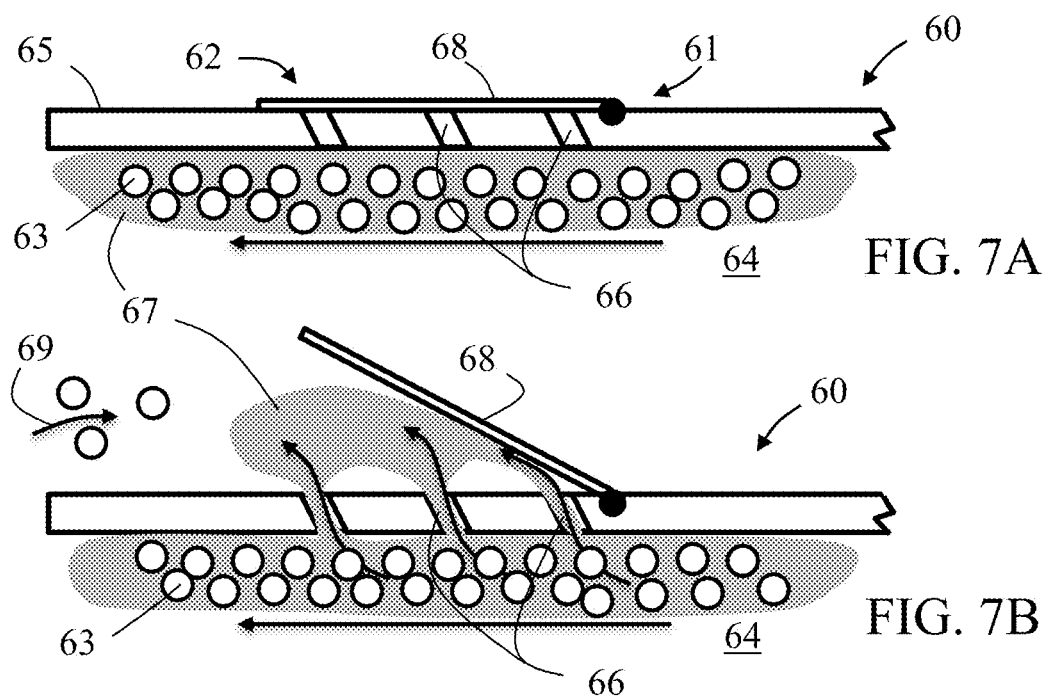
FIG. 7A
FIG. 7B
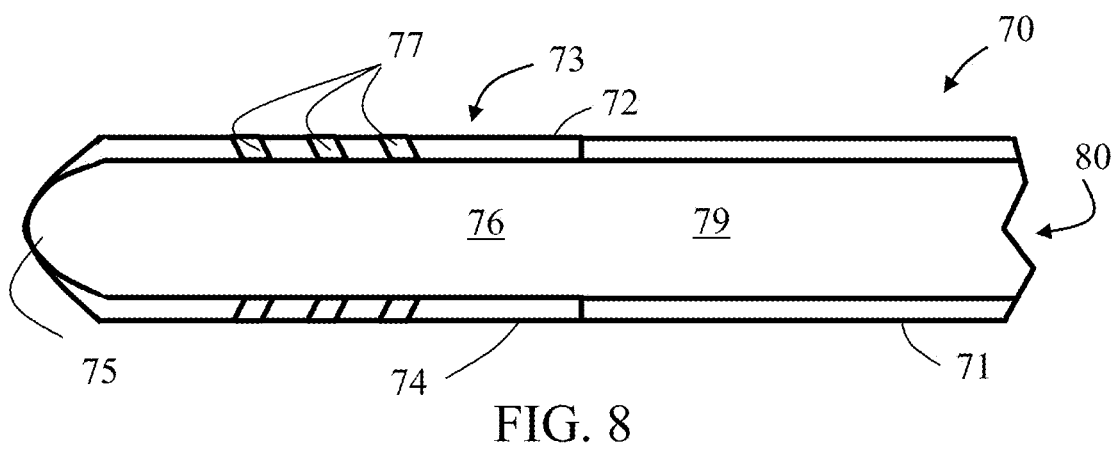
FIG. 8

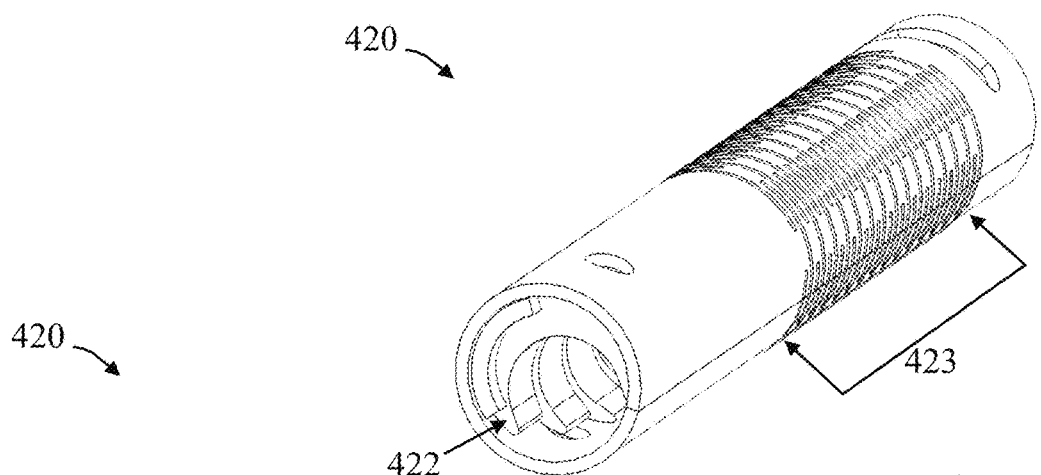
FIG. 19A
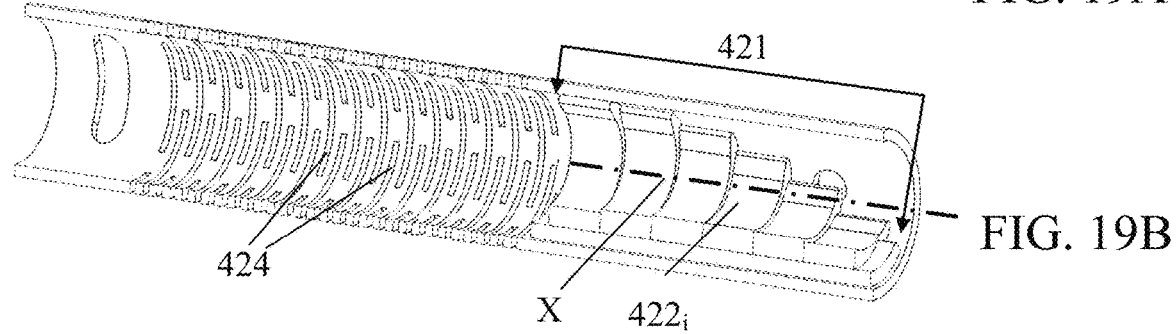
FIG. 19B
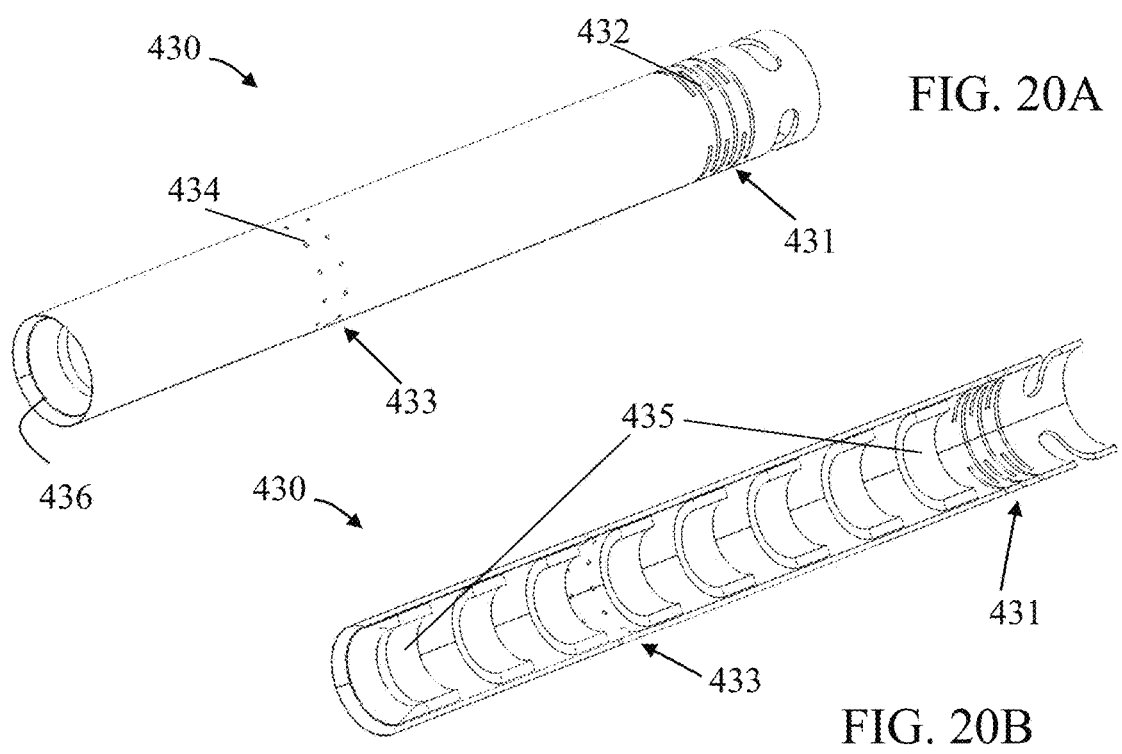
FIG. 20A
FIG. 20B

CATHETERS WITH SIDE OPENINGS FOR MODIFYING AND DELIVERING SUSPENSIONS TO A SUBJECT

RELATED APPLICATION

This application is a 35 U.S.C. § 371 national phase application of PCT/IB2016/051175, filed Mar. 2, 2016, which claims the benefit of priority under 35 USC 119(e) of U.S. Provisional Patent Application 62/127,036, filed on Mar. 2, 2015 entitled "Emobilization Microcatheter and Uses Thereof", the contents of which are incorporated herein by reference in their entirety.

FIELD OF THE INVENTION

The present invention, in some embodiments thereof, relates to catheters and methods for modifying a suspension of particles and for delivering the suspended particles to a target bodily part, for example, located within the cardiovascular system, of a subject. Some embodiments of the invention particularly relate to an embolization microcatheter and uses thereof in performing local embolization procedures, for example, for: (i) delivering embolization material in a small blood vessel towards a target bodily part, and (ii) performing local embolization in a small blood vessel feeding a (possibly, cancerous) target bodily part.

BACKGROUND OF THE INVENTION

The purpose of embolization is to prevent blood flow to an area of the body, which can effectively shrink a tumor or block an aneurysm, commonly carried out as an endovascular procedure. Access to the organ in question is acquired by means of a guidewire and catheter(s). The position of the correct artery or vein supplying the pathology in question can be located by digital subtraction angiography (DSA), producing images are then used as an accessing map to the correct vessel. The artificial embolus can be made by using coils, particles, foam, plug, microspheres or beads. Once the artificial emboli have been successfully introduced, another set of DSA images are taken to confirm a successful deployment.

Transarterial embolization therapy, tumor embolization, or transcatheter arterial embolization (TAE), involve administration of embolization material (which may include chemotherapeutics or/and radiotherapeutics) directly to a tumor typically associated with a target bodily part, such as an organ (for example, the liver), via a catheter. These techniques are usually performed using a microcatheter which targets the tumor, while attempting to avoid dispersion of embolization material to healthy organs.

Embolization of tumors is usually performed using microcatheters for different reasons. At first, there is a requirement for localized embolization for affecting primarily the tumor and as little healthy tissue as possible. One of the problems associated with embolization is commonly known as "non-target embolization", where the embolic material travels to small blood vessels other than to those which directly feed the target tumor or region. This can damage healthy tissues in these areas, often resulting in serious complications. Possible scenarios include gastric ulcers with liver embolization, as well as cases where embolic material refluxes alongside the microcatheter reaching the wall of the stomach, possibly causing ischemia and ulceration. An additional phenomenon, which is abundant, especially, in advanced stage liver cancer, is non-target embolization through arterioportal shunt.

A microcatheter is usually passed via a larger-lumen catheter, which is placed within the proximal part of the vessel, such as the celiac or hepatic artery, and the microcatheter is then advanced therethrough towards the tumor until reaching an effective distance for the embolization. In some scenarios, it is advantageous to use a diagnostic catheter as the delivery medium for the microcatheter, by not replacing it with a larger diameter sheath, for example, therefore saving substantial time. The inner lumen of the diagnostic catheter is very small, usually 0.035 and up to 0.038 inches, so that the microcatheter should be about 1 mm or less in outer diameter.

Another reason that microcatheters are routinely used in embolization procedures is the size of the feeding vessels, which carry blood directly to the organ and tumor. In order to get as close as possible to the tumor, the embolization catheter is advanced into smaller and sometimes tortuous vessels. Accessibility to these vessels is difficult, if not precluded, with a larger and often stiffer catheter. Also, blood vessels in the body tend to go into spasm when manipulated, causing an ineffective embolic material delivery, so flexible micro-sized catheters are preferred to avoid such scenarios.

SUMMARY OF THE INVENTION

The present invention, in some embodiments thereof, relates to catheters and methods for modifying a suspension of particles and for delivering the suspended particles to a target bodily part, for example, located within the cardiovascular system, of a subject. Some embodiments of the invention particularly relate to an embolization microcatheter and uses thereof in performing local embolization procedures. Some embodiments of the invention are applicable for increasing concentration of particles suspended in the suspension during delivery. Some embodiments of the invention are applicable for modifying flow characteristics (momentum) of the suspension during delivery. Some embodiments of the invention are applicable for: (i) delivering embolization material in a small blood vessel towards a target bodily part, and (ii) performing local embolization in a small blood vessel feeding a (possibly, cancerous) target bodily part, thereby forming emboli in small blood vessels, while preventing or minimizing non-target embolization.

According to an aspect of some embodiments of the present invention there is provided a catheter for modifying and delivering a suspension to a subject, the suspension includes particles suspended in a suspension fluid, the catheter comprising: a tubular wall comprising a proximal wall end, a distal wall end, and a lumen extending between the wall ends; the lumen is opened to a distal outlet at the distal wall end and to a proximal outlet proximally to the distal outlet, and is configured to allow passage therethrough of the suspension to the distal outlet; wherein the distal outlet is shaped or/and sized to allow passage therethrough of both the suspension fluid and the particles, and the proximal outlet is configured to allow passage therethrough of the suspension fluid without the particles and to block passage therethrough of the particles, during delivery of the suspension to the subject.

According to some embodiments of the invention, the proximal outlet includes a plurality of side openings distributed around or/and along a section of the tubular wall, wherein each side opening is shaped or/and sized to allow passage therethrough of the suspension fluid without the particles and to block passage therethrough of the particles, wherein at least one of the side openings has a smallest cross sectional dimension equal to or less than about 30 microns.

According to some embodiments of the invention, the suspended particles include solid embolic material or/and particulate embolic agent. According to some embodiments of the invention, the suspended particles include at least one of solid microspheres, embolic beads, chemotherapy beads, radioactive beads, radiopaque beads, and drug eluting beads. According to some embodiments of the invention, the suspension includes at least one of: a colloid, a hydrogel, an oil, lipiodol, a glue, an acrylic adhesive, and a cyanoacrylate-based glue. According to some embodiments of the invention, the suspension fluid includes at least one of: glucose, a contrast enhancing material, and saline.

According to some embodiments of the invention, the proximal outlet comprises at least one slit with a gap having a width less than a minimal diameter of the suspended particles, so as to facilitate the passage blocking. According to some embodiments of the invention, the at least one slit is a longitudinal slit extending with a length thereof parallel to a longitudinal axis of the catheter. According to some embodiments of the invention, the at least one slit is a circumferential slit extending with a length thereof vertically to a longitudinal axis of the catheter.

According to some embodiments of the invention, the catheter comprises a catheter length limiting rod-like element extending parallel to a catheter longitudinal axis across the proximal outlet, so as to resist or/and prevent elongation of the catheter about the proximal outlet. According to some embodiments of the invention, the rod-like element includes lateral extensions in a form of closed or/and opened rings curved in conformity to inner boundaries of the lumen.

According to some embodiments of the invention, the catheter comprises a flow restraining mechanism located in proximity to the distal outlet, and configured to modify flow of the suspension, so as to decrease horizontal velocity component of the suspended particles along a longitudinal axis of the catheter. According to some embodiments of the invention, the flow restraining mechanism comprises a helix positioned adjacent the distal outlet, and, shaped and dimensioned so as to increase lateral velocity component of the suspended particles and to decrease longitudinal velocity component of the suspended particles. According to some embodiments of the invention, the flow restraining mechanism comprises at least one inwardly radial projection originating from inner boundary of the lumen, configured to resist suspension flowing thereacross. According to some embodiments of the invention, the at least one inwardly radial projection include a plurality of longitudinally spaced opened or/and closed ring elements.

According to some embodiments of the invention, the proximal outlet comprises at least one pore having a diameter less than a minimal diameter of the suspended particles, thereby facilitating the passage blocking. According to some embodiments of the invention, the proximal outlet has a total opened cross section being equal to or greater than a smallest cross section of the lumen or/and a smallest cross section of the distal outlet. According to some embodiments of the invention, the proximal outlet is located at least 0.5 mm proximally to the distal outlet. According to some embodiments of the invention, the proximal outlet is located at least 2 mm proximally to the distal outlet.

According to some embodiments of the invention, the tubular wall section includes a valve mechanism comprising a cover configured to cover the proximal outlet and to prevent passage therethrough of fluids, and configured to uncover the proximal outlet when the tubular wall section is immersed in a proximally flowing fluid. According to some embodiments of the invention, a proximal portion of the tubular wall is connectable to a pressure source and a reservoir configured for supplying the suspension.

According to some embodiments of the invention, the catheter is configured as an embolization microcatheter.

According to some embodiments of the invention, the tubular wall outer diameter is equal to or less than about 4 mm. According to some embodiments of the invention, the tubular wall outer diameter is equal to or less than about 1 mm. According to some embodiments of the invention, the tubular wall is configured for insertion into a small blood vessel originating from a celiac or hepatic artery.

According to an aspect of some embodiments of the present invention there is provided a catheter for modifying and delivering a suspension to a subject, the suspension includes particles suspended in a suspension fluid, the catheter comprising: a catheter head comprising a tubular head wall including a proximal head end and a distal head end, the catheter head encloses a head lumen extending along the tubular head wall and opened to a distal outlet at the distal head end; a plurality of side openings distributed around or/and along a section of the tubular head wall proximally to the distal outlet; and a flexible tube connected to the proximal head end for integrating the head lumen with a tube lumen, provided along the flexible tube, into a catheter lumen configured to deliver the suspension; wherein the distal outlet is shaped or/and sized to allow passage therethrough of both the suspension fluid and the particles, and each side opening is shaped or/and sized to allow passage therethrough of the suspension fluid without the particles and to block passage therethrough of the particles, during delivery of the suspension to the subject.

According to some embodiments of the invention, the catheter is configured as an embolization microcatheter.

According to some embodiments of the invention, the at least one of the side openings comprises a pore having a cross sectional dimension less than a minimal diameter of the suspended particles. According to some embodiments of the invention, each of the side openings has a smallest cross sectional dimension equal to or less than 100 micrometers. According to some embodiments of the invention, the side openings are formed by one of laser cutting (femtolaser for polymers), laser drilling, etching, skiving (for polymers) and EDM, or any combination thereof. According to some embodiments of the invention, the head wall is made of a metallic material, a polymeric material, or a combination thereof, and the tube is made of a flexible polymeric material.

According to an aspect of some embodiments of the present invention there is provided a catheter head for delivering a suspension to a subject, the suspension includes particles suspended in a suspension fluid, the catheter comprising: a rigid tubular head wall comprising a proximal head end and a distal head end and enclosing a head lumen extending along the head wall, the head lumen is opened to a distal outlet at the distal head end and to a plurality of side openings distributed around or/and along a section of the head wall proximally to the distal outlet; wherein the catheter head is connectable, at the proximal head end, to a catheter body comprising a flexible tube, for integrating the head lumen with a tube lumen into a catheter lumen configured to deliver the suspension; wherein the distal outlet is shaped or/and sized to allow passage therethrough of both the suspension fluid and the particles, and each side opening is shaped or/and sized to allow passage therethrough of the suspension fluid without the particles and to block passage therethrough of the particles, during delivery of the suspension to the subject.

According to some embodiments of the invention, the catheter head is configured as an embolization microcatheter, when connected with the catheter body. According to some embodiments of the invention, the at least one of the side openings comprises a pore having a cross sectional dimension less than a minimal diameter of the suspended particles.

According to an aspect of some embodiments of the present invention there is provided a catheter connectable to a suspension reservoir containing premade suspension of particles suspended in a suspension fluid, the catheter comprising: a tubular wall comprising a proximal wall end, a distal wall end, and a lumen opened to a proximal inlet at the proximal wall end and to a distal outlet at the distal wall end, the tubular wall is configured to facilitate the lumen to be in fluid communication with the premade suspension via the proximal inlet, when the catheter is connected to the suspension reservoir; and a suspension concentrating mechanism, located between the proximal inlet and the distal outlet, and configured for increasing concentration of the particles suspended in the premade suspension by removing an excess volume of the suspension fluid, without the suspended particles, from the premade suspension, thereby leaving a chosen remaining volume of concentrated suspension between the suspension concentrating mechanism and the distal outlet.

According to some embodiments of the invention, the catheter is an embolization microcatheter configured for delivering the concentrated suspension into a small blood vessel via the distal outlet.

According to some embodiments of the invention, the suspension concentrating mechanism includes a suspension filter configured to block passage therethrough of the suspended particles and to allow passage therethrough of the suspension fluid without the particles. According to some embodiments of the invention, the catheter with the concentrating mechanism is configured to disperse the removed excess volume of the suspension fluid through a proximal outlet located at the tubular wall proximally to the distal outlet.

According to some embodiments of the invention, the proximal outlet includes a plurality of side openings.

According to some embodiments of the invention, the excess volume is at least about 50% of total volume of the suspension fluid. According to some embodiments of the invention, the excess volume is about 80% of total volume of the suspension fluid.

According to some embodiments of the invention, the catheter is configured for delivering the concentrated suspension in an outlet flow rate being at least half an inlet flow rate of the premade suspension flowing into the proximal inlet. According to some embodiments of the invention, the catheter is configured such that the flow rates ratio of the excess volume, deliverable through the proximal outlet, to the remaining volume, deliverable through the distal outlet, is at least 2, optionally particularly at least 4, optionally particularly at least 8.

According to an aspect of some embodiments of the present invention there is provided a catheter connectable to a suspension reservoir containing premade suspension of particles suspended in a suspension fluid, the catheter comprising: a tubular wall comprising a proximal wall end, a distal wall end, and a lumen opened to a proximal inlet at the proximal wall end and to a distal outlet at the distal wall end, the tubular wall is configured to facilitate the lumen to be in fluid communication with the premade suspension via the proximal inlet, when the catheter is connected to the suspension reservoir; and a flow restraining mechanism, located between the proximal inlet and the distal outlet, and configured for removing an excess mass from an incoming suspension having a first momentum, thereby leaving a remaining mass of concentrated suspension, between the flow restraining mechanism and the distal outlet, having a chosen second momentum being substantially smaller than the first momentum.

According to some embodiments of the invention, the catheter is an embolization microcatheter configured for delivering the concentrated suspension into a small blood vessel via the distal outlet.

According to some embodiments of the invention, the flow retaining mechanism includes a suspension filter configured to block passage therethrough of the suspended particles and to allow passage therethrough of the suspension fluid without the particles. According to some embodiments of the invention, the catheter with the flow retaining mechanism is configured to disperse the removed excess mass of the incoming suspension through a proximal outlet located at the tubular wall proximally to the distal outlet.

According to some embodiments of the invention, the proximal outlet includes a plurality of side openings. According to some embodiments of the invention, the catheter is configured such that a mass ratio between the excess mass and the remaining mass is at least 2.

According to some embodiments of the invention, the catheter is configured such that a momentum ratio between the first momentum and the second momentum is at least 3, optionally particularly at least 9, optionally particularly at least 20, optionally particularly at least 30. According to some embodiments of the invention, the catheter is configured for delivering the concentrated suspension via the distal outlet at a delivery velocity having a horizontal component being approximately 50 cm/second or less, optionally particularly approximately 20 cm/second or less, optionally particularly approximately 5 cm/second or less.

According to an aspect of some embodiments of the present invention there is provided a method for modifying and delivering a suspension into a blood vessel of a subject, the suspension includes particles suspended in a suspension fluid, the method comprising: providing a catheter having a proximal inlet, a distal outlet, and a proximal outlet located between the proximal inlet and the distal outlet; positioning the distal outlet adjacent a target location in the blood vessel; injecting into the proximal inlet a premade suspension of the particles suspended in a total volume of the suspension fluid; allowing an excess volume of the suspension fluid with the suspended particles to disperse via the proximal outlet; and delivering into the blood vessel, via the distal outlet, a remaining volume of the suspension fluid with the suspended particles.

According to some embodiments of the invention, the allowing includes filtering the premade suspension. According to some embodiments of the invention, the filtering includes blocking passage of the suspended particles through the proximal opening.

According to some embodiments of the invention, the method further comprises reducing a velocity of the suspension fluid between the proximal inlet and the distal outlet by half or less. According to some embodiments of the invention, the method further comprises reducing a velocity of the suspension fluid between the proximal outlet and the distal outlet by half or less. According to some embodiments of the invention, the method further comprises reducing a momentum of the suspension fluid between the proximal inlet and the distal outlet by ninth or less. According to some embodiments of the invention, the method further comprises reducing a momentum of the suspension fluid between the proximal outlet and the distal outlet by eighth or less.

According to some embodiments of the invention, the method further comprises reducing a mass of the suspension fluid between the proximal outlet and the distal outlet by half or less. According to some embodiments of the invention, the method further comprises reducing a flow rate of the suspension fluid between the proximal outlet and the distal outlet by fourth or less. According to some embodiments of the invention, the volumetric ratio between the total volume and the remaining volume is at least four. According to some embodiments of the invention, the delivering of the remaining volume of the suspension fluid has a velocity of 20 cm/second or less.

According to an aspect of some embodiments of the present invention there is provided a method for performing local embolization in a small blood vessel feeding a cancerous target bodily part of a subject, the method comprising: providing an embolization microcatheter having a distal outlet, a proximal inlet, and a proximal outlet located between the proximal inlet and the distal outlet; positioning the distal outlet in the small blood vessel upstream to the cancerous target bodily part; injecting into the proximal inlet a premade suspension of particles suspended in a suspension fluid; allowing an excess volume of the suspension fluid with the suspended particles to disperse via the proximal outlet and blocking the particles from passing through the proximal outlet; and delivering into the small blood vessel a remaining volume of the suspension fluid with the suspended particles, at least until creating an embolus sized for effective blocking of blood flow between the distal outlet and the cancerous target bodily part. According to some embodiments of the invention, the suspension fluid includes a contrast enhancing agent.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings/images:

FIGS. 7A-7B are schematic partial sectional orthogonal views of exemplary embodiments of a portion of an infusion agent (e.g., suspended particle) flow disruption section that includes a covering mechanism, before (FIG. 4A) and after (FIG. 4B) actuation thereof, in accordance with some embodiments of the invention;

FIG. 8 is a schematic sectional orthogonal view of an exemplary embodiment of a catheter including a flexible tube connected to a proximal end of a tip, in accordance with some embodiments of the invention;

FIGS. 19A-19B illustrate an isometric view of an exemplary embodiments of a catheter head including a plurality of staggered lines of circumferential slits and an oblique helix (FIG. 19A), and a sectional orthogonal view of the catheter head (FIG. 19B), in accordance with some embodiments of the invention;

FIGS. 20A-20B illustrate an isometric view of an exemplary embodiments of a catheter head including a first section of circumferential slits and a second section of pores, and a plurality of inwardly radial projections (FIG. 20A), and a sectional orthogonal view of the catheter head (FIG. 20B), in accordance with some embodiments of the invention.

DESCRIPTION OF SPECIFIC EMBODIMENTS OF THE INVENTION

Figure 1A:
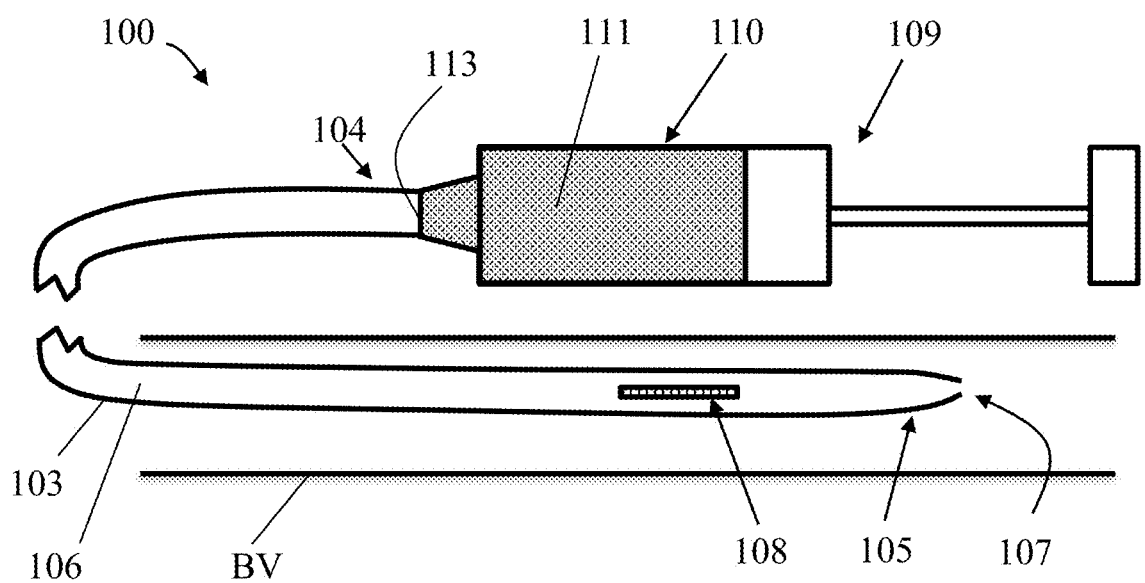
FIGS. 1A-1B are schematic sectional orthogonal views of an exemplary embodiment of a catheter before (FIG. 1A) and after (FIG. 1B) modifying and delivering a suspension, in accordance with some embodiments of the invention.

The present invention, in some embodiments thereof, relates to microcatheters and methods for modifying a suspension of particles and for delivering the suspended particles to a target bodily part, for example, located within the cardiovascular system, of a subject. Some embodiments particularly relate to an embolization microcatheter and uses thereof in performing local embolization procedures. Some embodiments of the invention are applicable for increasing concentration of particular suspended in the suspension during delivery. Some embodiments of the invention are applicable for modifying flow characteristics (momentum) of the suspension during delivery. Some embodiments of the invention are applicable for: (i) delivering embolization material in a small blood vessel towards a target bodily part, and (ii) performing local embolization in a small blood vessel feeding a (possibly, cancerous) target bodily part, thereby forming emboli in small blood vessels, while preventing or minimizing non-target embolization.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. The following exemplary embodiments may be described in the context of exemplary embolization procedures for ease of description and understanding. However, the invention is not limited to the specifically described devices and methods, and may be adapted to various clinical applications without departing from the overall scope of the invention.

In view of the preceding, and other, limitations associated with current embolization techniques, there is need for developing and practicing improved or/and new techniques (devices and methods) for delivering particles (e.g., including embolization material or/and contrast enhancing material) into small blood vessels located in close proximity to a target body part, while preventing or diminishing particles' back flow or reflux from the small blood vessels.

The term "suspension", as used herein, refers to a mixture of solid particles floating or/and dispersed in a fluid (ordinarily, a liquid). As used, and referred to, herein, a suspension is suitable for being supplied to, or provided in, a reservoir of a catheter and infused (such as by injection) into a blood vessel of a (human or animal) subject. The term "suspension", as used, and referred to, herein, is interchangeable with the term "infusion suspension".

The terms "particles", "beads" and "infusion agent", as used herein, refer to a particulate substance that can be suspended (dispersed) in a suspension (dispersion) fluid for forming a suspension (an infusion suspension).

In exemplary embodiments, particles are composed of, or include, embolization (embolic) material or/and contrast media (such as contrast enhancing material or agent). In exemplary embodiments, the infusion agent is composed of, or includes, embolization (embolic) material, wherein the embolization material, in addition to having embolization properties, also has radio-opacity or/and radiographic properties. In exemplary embodiments, the infusion agent is composed of, or includes, contrast enhancing material, wherein the contrast enhancing material, in addition to having radio-opacity or/and radiographic properties, also has embolization properties. In exemplary embodiments, the particles may be composed of, or include, any type or kind, and amount, of other material, having any type or kind of properties, suitable for infusing into a blood vessel of a subject.

In exemplary embodiments, the (infusion) suspension (including the particles suspended in the (infusion) fluid may be composed and formulated for being suitable in embolic type therapies, for example, intra-arterial embolic therapies. In some such embodiments, the (infusion) suspension may include the suspended infusion agent in the form of embolic beads for bland embolization. Optionally, alternatively or additionally, the infusion suspension may include the suspended infusion agent in the form of lipidol mixed with chemotherapeutic agents and embolic beads or/and chemotherapy drug eluting beads (e.g., polyvinyl alcohol microspheres loaded with doxorubicin, superabsorbent polymer microspheres—loaded with doxorubicin, or gelatin microspheres—loaded with cisplatin) for chemo-embolization. Optionally, alternatively or additionally, the infusion suspension may include the suspended infusion agent in the form of radioactive beads for radio-embolization.

In exemplary embodiments, embolization material may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). Embolization material may include radiopaque beads or/and drug eluting beads.

In exemplary embodiments, the suspension fluid includes a contrast enhancing material (agent), for example, diluted to a certain degree such as with saline. In some instances, the medical practitioner may mix together a viscous contrast enhancing material (agent) with embolization materials including saline and embolization beads (particles) or/and chemotherapeutic beads (particles), for example in a volumetric ratio of 50:50, thereby producing a fluidic suspension of beads and contrast enhancing material (agent) diluted to a chosen degree. In an exemplary embodiment, the suspension includes drug-eluting beads (DEB), chemotherapeutic material (e.g., doxorubicin) and contrast enhancing material. In exemplary embodiments, the contrast enhancing material (agent) may be, or include, any of various different types or kinds of contrast media, for example, Visipaque™ (iodixanol), or Omnipaque™ (iohexol), among many other suitable types and kinds of contrast media.

In a non-limiting manner, numerous other possible compositions and formulations of the (infusion) suspension, in general, and of the particles, of the beads, of the infusion agent, and of the (infusion) suspension fluid, in particular, are applicable for implementing embodiments of the invention.

An aspect of some embodiments of the present invention is a catheter for modifying and delivering a suspension to a subject.

In exemplary embodiments of such an aspect, the catheter includes a tubular wall having a proximal wall end, a distal wall end, and a lumen extending between the wall ends. The lumen is opened to a distal outlet at the distal wall end and to a proximal outlet proximally to the distal outlet, and is configured to allow passage therethrough of the suspension to the distal outlet. The distal outlet is shaped or/and sized to allow passage therethrough of both the suspension fluid and the particles, and the proximal outlet is configured to allow passage therethrough of the suspension fluid without the particles and to block passage therethrough of the particles.

In alternative exemplary embodiments of such an aspect, the catheter includes a catheter head having a tubular head wall including a proximal head end and a distal head end. The catheter head encloses a head lumen extending along the tubular head wall and opened to a distal outlet at the distal head end. The catheter also includes a plurality of side openings distributed around or/and along a section of the tubular head wall proximally to the distal outlet, and a flexible tube connected to the proximal head end for integrating the head lumen with a tube lumen, provided along the flexible tube, into a catheter lumen configured to deliver the suspension. The distal outlet is shaped or/and sized to allow passage therethrough of both the suspension fluid and the particles, and each side opening is shaped or/and sized to allow passage therethrough of the suspension fluid without the particles and to block passage therethrough of the particles, during delivery of the suspension to the subject.

An aspect of some embodiments of the present invention is a catheter head for delivering a suspension to a subject. In exemplary embodiments of such an aspect, the catheter includes a rigid tubular head wall having a proximal head end and a distal head end and enclosing a head lumen extending along the head wall. The head lumen is opened to a distal outlet at the distal head end and to a plurality of side openings distributed around or/and along a section of the head wall proximally to the distal outlet. The catheter head is connectable, at the proximal head end, to a catheter body having a flexible tube, for integrating the head lumen with a tube lumen into a catheter lumen configured to deliver the suspension. The distal outlet is shaped or/and sized to allow passage therethrough of both the suspension fluid and the particles, and each side opening is shaped or/and sized to allow passage therethrough of the suspension fluid without the particles and to block passage therethrough of the particles, during delivery of the suspension to the subject.

An aspect of some embodiments of the present invention is a catheter connectable to a suspension reservoir containing premade suspension of particles suspended in a suspension fluid.

In exemplary embodiments of such an aspect, the catheter includes a tubular wall having a proximal wall end, a distal wall end, and a lumen opened to a proximal inlet at the proximal wall end and to a distal outlet at the distal wall end. The tubular wall is configured to facilitate the lumen to be in fluid communication with the premade suspension via the proximal inlet, when the catheter is connected to the suspension reservoir. The catheter also includes a suspension concentrating mechanism, located between the proximal inlet and the distal outlet, and configured for increasing concentration of the particles suspended in the premade suspension by removing an excess volume of the suspension fluid, without the suspended particles, from the premade suspension, thereby leaving a chosen remaining volume of concentrated suspension between the suspension concentrating mechanism and the distal outlet.

In alternative exemplary embodiments of such an aspect, the catheter includes a tubular wall having a proximal wall end, a distal wall end, and a lumen opened to a proximal inlet at the proximal wall end and to a distal outlet at the distal wall end. The tubular wall is configured to facilitate the lumen to be in fluid communication with the premade suspension via the proximal inlet, when the catheter is connected to the suspension reservoir. The catheter also includes a flow restraining mechanism, located between the proximal inlet and the distal outlet, and configured for removing an excess mass from an incoming suspension having a first momentum, thereby leaving a remaining mass of concentrated suspension, between the flow restraining mechanism and the distal outlet, having a chosen second momentum being substantially smaller than the first momentum.

An aspect of some embodiments of the present invention is a method for modifying and delivering a suspension into a blood vessel of a subject. In exemplary embodiments of such an aspect, the method includes: providing a catheter having a proximal inlet, a distal outlet, and a proximal outlet located between the proximal inlet and the distal outlet; positioning the distal outlet adjacent a target location in the blood vessel; injecting into the proximal inlet a premade suspension of the particles suspended in a total volume of the suspension fluid; allowing an excess volume of the suspension fluid with the suspended particles to disperse via the proximal outlet; and delivering into the blood vessel, via the distal outlet, a remaining volume of the suspension fluid with the suspended particles.

An aspect of some embodiments of the present invention is a method for performing local embolization in a small blood vessel feeding a cancerous target bodily part of a subject. In exemplary embodiments of such an aspect, the method includes: providing an embolization microcatheter having a distal outlet, a proximal inlet, and a proximal outlet located between the proximal inlet and the distal outlet; positioning the distal outlet in the small blood vessel upstream to the cancerous target bodily part; injecting into the proximal inlet a premade suspension of particles suspended in a suspension fluid; allowing an excess volume of the suspension fluid with the suspended particles to disperse via the proximal outlet and blocking the particles from passing through the proximal outlet; and delivering into the small blood vessel a remaining volume of the suspension fluid with the suspended particles, at least until creating an embolus sized for effective blocking of blood flow between the distal outlet and the cancerous target bodily part.

The preceding aspects of exemplary embodiments of the present invention, and characteristics and features thereof, are better understood with reference to the following illustrative description and accompanying drawings. Throughout the following illustrative description and accompanying drawings, same reference notation and terminology (i.e., numbers, letters, symbols) are consistently used and refer to same structures, components, elements, steps or procedures, or/and features. It is to be understood that the invention is not necessarily limited in its application to particular details of construction or/and arrangement of catheter device or apparatus components, or to any particular sequential ordering of method steps or procedures, set forth in the following illustrative description. The invention is capable of other embodiments or of being practiced or carried out in various ways.

Figure 1B:
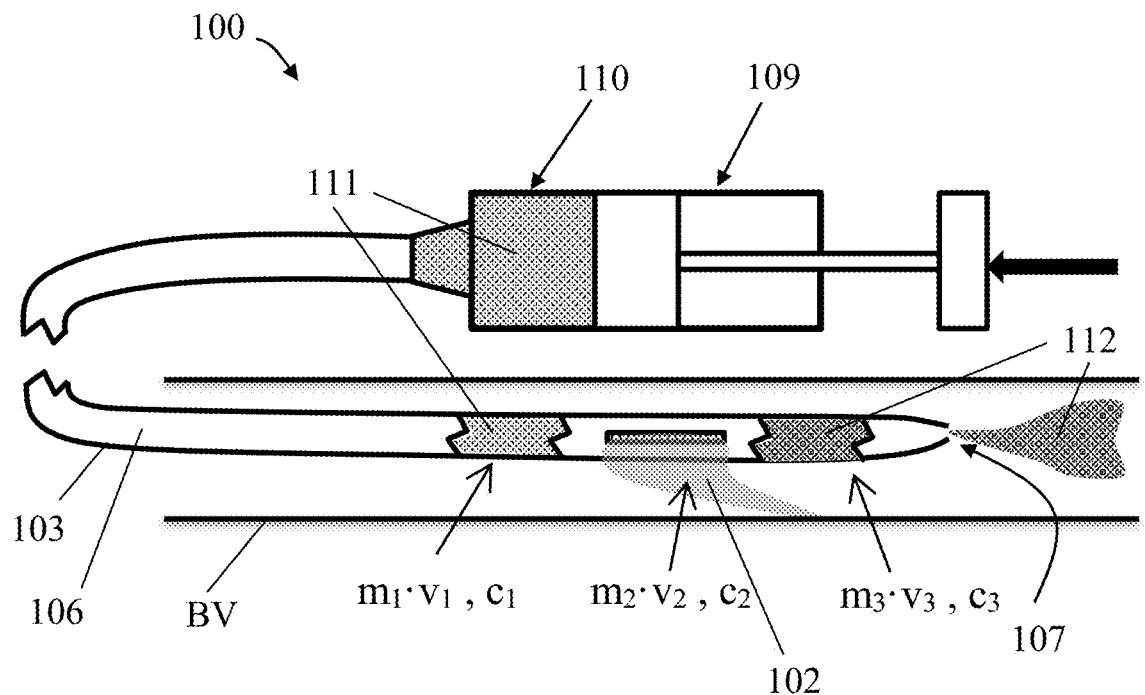

FIGS. 1A-1B are schematic orthogonal views of a catheter 100 before (FIG. 1A) and after (FIG. 1B) modifying and delivering a suspension of particles in a suspension fluid. Catheter 100 includes tubular wall 103 having a proximal wall end 104, a distal wall end 105, and a lumen 106 extending between wall ends 104 and 105. Lumen 106 is opened to a distal outlet 107 at distal wall end 105, and to a proximal outlet 108 located proximally to distal outlet 107. The catheter is configured to deliver the suspension via lumen 106 to distal outlet 107, therefore distal outlet 107 is shaped or/and sized to allow passage therethrough of the suspension fluid and the particles.

A proximal wall end 104 of the catheter is connectable to a pressure source 109 and a suspension reservoir 110, configured for supplying the suspension. In some embodiments, catheter 100 includes a single lumen, namely lumen 106. Tubular wall 103 outer diameter is optionally equal to or less than about 4 mm. The catheter is optionally configured as an embolization microcatheter. In some such embodiments, tubular wall 103 outer diameter is optionally equal to or less than about 1 mm or/and configured for insertion into a small blood vessel BV, such as one originating from a celiac or hepatic artery. In some embodiments, catheter 100 has an external diameter equal to the diameter of a commercially available microcatheter, such as a 2.1 French catheter, or a 2.7 French catheter, or a 2.9 French catheter.

The particles may include solid embolic material or/and particulate embolic agent, or/and may include at least one of solid microspheres, embolic beads, chemotherapy beads, radioactive beads, radiopaque beads, and drug eluting beads. The suspension may include includes at least one of colloid, hydrogel, oil, lipiodol, glue, acrylic adhesive, and cyanoacrylate-based glue, whereas the suspension fluid may include glucose, a contrast enhancing material or/and saline.

In some embodiments, proximal outlet 108 is configured to allow passage therethrough of the suspension fluid without the particles and to block passage therethrough of the particles, for example, during delivery of the suspension to a subject. Proximal outlet 108 optionally includes a plurality of side openings, each is shaped or/and sized to allow passage therethrough of the suspension fluid without the particles and to block passage therethrough of the particles, for example, during delivery of the suspension to the subject. In some embodiments, at least one of the side openings has a smallest cross sectional dimension equal to or less than about 30 microns, optionally equal to or less than about 40 microns, optionally equal to or less than about 100 microns, optionally equal to or less than about 500 microns, or higher, or lower, or intermediate size. Proximal outlet 108 may include at least one pore having a diameter less than a minimal diameter of the particles, thereby facilitating blocking of the particles.

In some embodiments, catheter 100 is particularly applicable for delivering suspension of particles in the suspension fluid, into blood vessel BV. Distal outlet 107 of catheter 100 may be first positioned adjacent a target location in blood vessel BV. Then, premade suspension 111 of the particles can be injected into proximal inlet 113. By allowing an excess volume 102 of the suspension fluid to disperse via proximal outlet 108, catheter 100 can be used for delivering the particles with the remaining volume of the suspension fluid via distal outlet 107.

Proximal outlet 108 can be configured particularly and used for filtering premade suspension 111, optionally, by including blocking passage of the particles through proximal opening 108.

Optionally, additionally or alternatively, proximal outlet 108 can be configured and used for reducing a velocity of the suspension fluid between proximal inlet 113 and distal outlet 107, optionally, between proximal outlet 108 and distal outlet 107, by half or less.

Optionally, additionally or alternatively, proximal outlet 108 can be configured and used for reducing momentum of the suspension fluid between proximal inlet 113 and distal outlet 107 by a ninth or less, or/and optionally, for reducing momentum of the suspension fluid between proximal outlet 108 and distal outlet 107 by an eighth or less.

Optionally, additionally or alternatively, proximal outlet 108 can be configured and used for reducing mass of the suspension fluid between proximal outlet 108 and distal outlet 107 by half or less.

In some embodiments, flow rate of the suspension fluid between proximal outlet 108 and distal outlet 107 is reduced by a fourth or less. In some embodiments, the volumetric ratio between total volume of injected premade suspension 111 and the remaining volume is 4 or more. In some embodiments, the particles with the remaining volume of the suspension fluid is delivered via distal outlet 107 at a velocity of 20 cm/second or less.

In some embodiments, catheter 100 is particularly applicable for performing local embolization in a small blood vessel feeding a cancerous target bodily part, optionally when in a form and size of an embolization microcatheter. Distal outlet 107 of the catheter may first be positioned in the small blood vessel upstream to the cancerous target bodily part. Then, premade suspension 111 of the particles in the suspension fluid can be injected into proximal inlet 113. By allowing an excess volume 102 of the suspension fluid to disperse via proximal outlet 108, and blocking the particles from passing through proximal outlet 107, catheter 100 can be used for delivering the particles with a remaining volume of the suspension fluid at least until creating an embolus sized for effective blocking of blood flow between the distal outlet and the cancerous target bodily part. In some such embodiments, the suspension fluid may be or include a contrast enhancing agent.

In some embodiments, proximal outlet 108 has a total opened cross section being equal to or greater than a smallest cross section of lumen 106 or/and distal outlet 107. Optionally, total opened cross section of proximal outlet 108 is at least 2 times, optionally at least 5 times, optionally at least 10 times greater than minimal cross section of lumen 106 or/and distal outlet 107. In some embodiments, total opened cross section of proximal outlet 108 is at least about 0.5 mm², optionally at least about 1 mm², optionally at least about 1.5 mm², optionally at least about 2 mm². In some embodiments, minimal cross section of lumen 106 or/and of distal outlet 107 is about 0.5 mm² or less, optionally about 0.25 mm² or less, optionally about 0.15 mm² or less.

In some embodiments, proximal outlet 108 is located at least 0.5 mm proximally to distal outlet 107, optionally with a distal-most side opening thereof. In some embodiments, proximal outlet 108 is located at least 2 mm proximally to distal outlet 107.

In some embodiments, suspension reservoir 110 contains a premade suspension 111 of the particles in the suspension fluid 102. Tubular wall 103 is configured to arrange lumen 106 into fluid communication with the premade suspension 111 via a proximal inlet 113 located at proximal wall end 104, when the catheter is connected to the suspension reservoir.

In some embodiments, catheter 100 with proximal outlet 108 is configured as a suspension concentrating mechanism for removing an excess volume 102 of the suspension fluid from the premade suspension 111 via the proximal outlet 108, thereby leaving a chosen remaining volume of concentrated suspension 112 between the suspension concentrating mechanism (proximal outlet 108) and distal outlet 107. As such, proximal outlet 108 may further be configured as a suspension filter by blocking passage therethrough of the particles and allowing passage therethrough of suspension fluid. In some embodiments, particles concentration $c_1$ in the premade suspension 111 is about 25% or less, optionally about 10% (e.g., suspension reservoir 110 is filled with about 10 cc of premade suspension 111, including 2 cc of beads mixed with 8 cc of suspension fluid). In some embodiments, particles concentration $c_3$ in the concentrated suspension 112 is greater than about 25%, optionally about 30% or more, optionally about 50% or more. Optionally, the excess volume is at least about 30%, optionally at least about 50%, optionally about 80%, of total volume of the suspension fluid. In some embodiments, all particles are blocked from passing through proximal outlet 108 so particles concentration $c_2$ there is null, although in some other embodiments some particles pass through proximal outlet 108, and in some such other embodiments, particles concentration is about 10% or less, optionally about 5% or less.

In some embodiments, catheter 100 with proximal outlet 108 is configured as a flow restraining mechanism for removing an excess mass $m_2$ in velocity $v_2$, from an incoming (premade) suspension 111 having a first momentum $m_1 \cdot v_1$, thereby leaving a remaining mass $m_3$ of concentrated suspension 112, between the flow restraining mechanism (proximal outlet 108) and distal outlet 107, having a chosen second momentum $m_3 \cdot v_3$ being substantially smaller than first momentum $m_1 \cdot v_1$.

In some embodiments, catheter 100 is configured for delivering concentrated suspension 112 in an outlet flow rate being at least half an inlet flow rate of premade suspension 111 flowing into proximal inlet 113. A flow rates ratio of the excess volume 102, deliverable through proximal outlet 108, to the remaining volume, deliverable through distal outlet 107, is at least 2, optionally particularly at least 4, optionally particularly at least 8.

For illustrative purposes, FIG. 1B shows a first cutaway portion of catheter 100 proximally and adjacent to the proximal outlet 108, and a second cutaway portion of catheter 100 distally and adjacent to the proximal outlet 108, for demonstrating difference of momenta and concentration of a deliverable particles quantity, before and after passing though proximal outlet 108.

In some embodiments, catheter 100 is configured such that a mass ratio between the excess mass $m_2$ and remaining mass $m_3$ is at least 2, optionally at least 4. In some embodiments, catheter 100 is configured such that a momentum ratio between first momentum $m_1 \cdot v_1$ and second momentum $m_3 \cdot v_3$ is at least 3, optionally particularly at least 9, optionally particularly at least 20, optionally particularly at least 30.

Inlet flow rate (of premade suspension 111 flowing into proximal inlet 113) may be within the range of 1-10 cc/minute, optionally about 2 cc/minute, or optionally about 5 cc/minute. Flow rate of the excess volume 102 of the suspension fluid, via proximal outlet 108, is optionally at least 0.5 cc/minute, optionally at least 1.5 cc/minute, or optionally 3 cc/minute. Flow rate of the concentrated suspension 112, via distal outlet 107, is optionally about 1 cc/minute or less, or optionally about 0.5 cc/minute or less. In some embodiments, concentrated suspension 112 is delivered via distal outlet 107 at a delivery velocity having a horizontal component being approximately 50 cm/second or less, optionally particularly approximately 20 cm/second or less, optionally particularly approximately 5 cm/second or less.

In some scenarios, there is a requirement to affect a flow of suspension in a catheter (e.g., catheter head, in particular), of the present invention, so that the flow rate or/and velocity of the suspension fluid dispersing through the proximal outlet (e.g., side openings) will be substantially greater than flow rate or/and velocity of the suspension (particles with remaining suspension fluid) at the exit of the distal outlet. Some of such scenarios may benefit from having a low flow rate or/and velocity at distal outlet so that particles will immerse with the surrounding blood flow in the target blood vessel and will have a flow rate after exit close or substantially the same as surrounding blood flow rate. In some such or other scenarios, it may be beneficial to disperse the suspension fluid through the proximal outlet in a high flow rate or/and velocity relatively to surrounding blood flow rate, in order to cause local disturbance (e.g., vortex or/and turbulence) in effort to resist flow of particles thereacross in general direction from distal outlet to proximal outlet (such as in case of backflow/reflux of blood or/and particles).

Figure 2A:
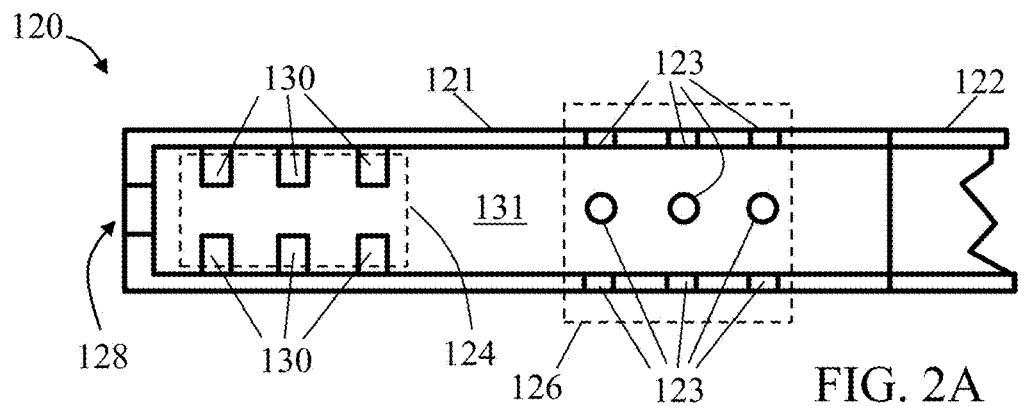
FIGS. 2A-2B are schematic sectional orthogonal views of an exemplary embodiment of a catheter with side openings and a flow restraining mechanism, before (FIG. 1A) and after (FIG. 1B) modifying and delivering a suspension, in accordance with some embodiments of the invention.
Figure 2B:
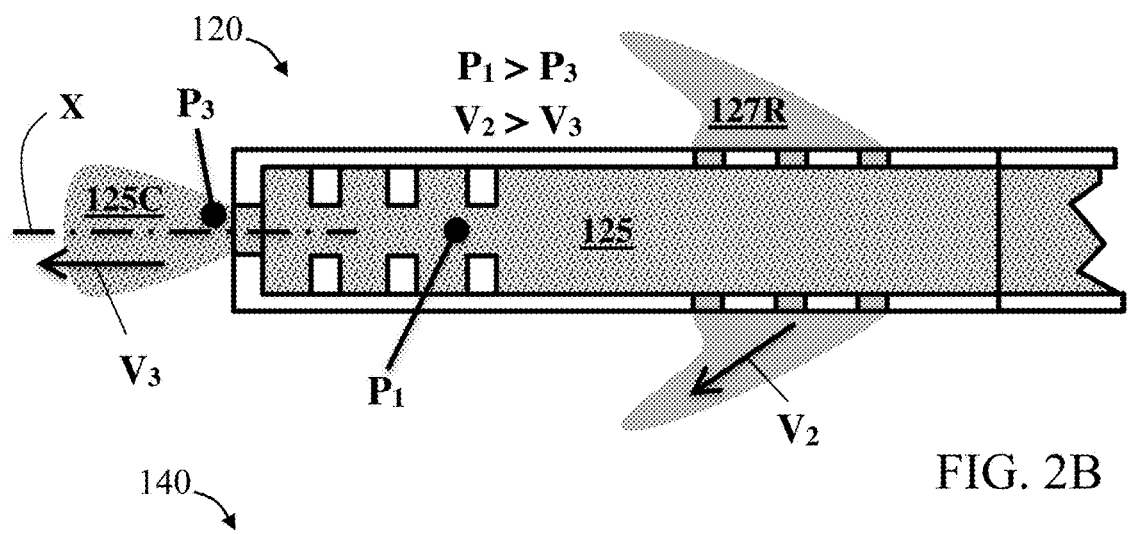
Figure 3:
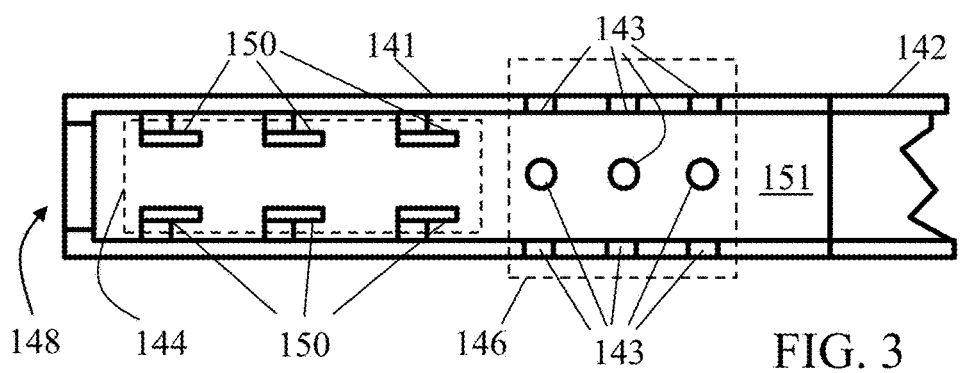
FIG. 3 is a schematic sectional orthogonal view of an exemplary embodiment of a catheter with a flow restraining mechanism including of a plurality of concave orifices, in accordance with some embodiments of the invention.
Figure 4:
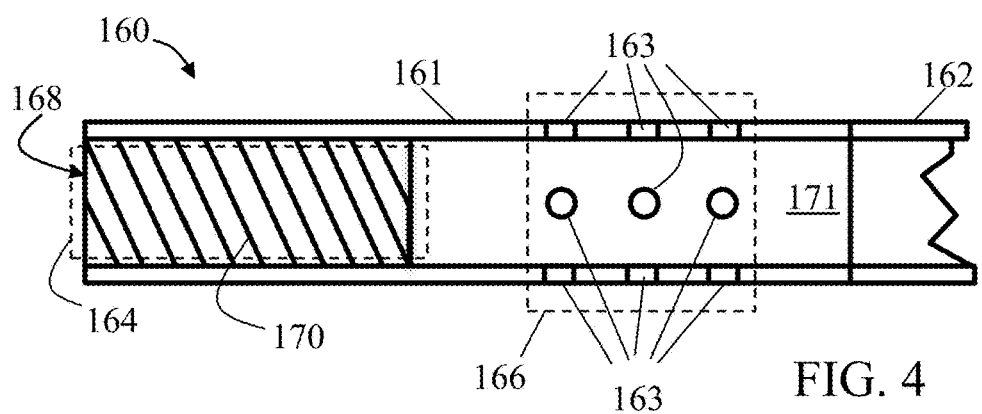
FIG. 4 is a schematic sectional orthogonal view of an exemplary embodiment of a catheter with a flow restraining mechanism including of a helix, in accordance with some embodiments of the invention.

In some embodiments, a flow restraining mechanism is used in the lumen of the catheter head and configured for resisting suspension flow in the lumen section between the proximal outlet and the distal outlet. Optionally, alternatively or additionally, the flow restraining mechanism is used and configured to increase pressure inside the catheter head and adjacent distal outlet in order to diminish/choke the flow at exit there, therefore, increasing exit velocity at the proximal outlet (optionally, in accordance with the Venturi Effect)
. FIGS. 2A-2B are schematic sectional orthogonal views of an exemplary embodiment of a catheter 120 (formed by a catheter head 121 connected to a flexible tube 122) with a proximal outlet 126 (area) in a form of (or including) side openings 123, and a flow restraining mechanism 124, before (FIG. 1A) and after (FIG. 1B) modifying and delivering a suspension 125 (including particles suspended in a suspension fluid). Catheter 120 is optionally similar or even identical in design or/and configuration to catheter 100, and is optionally in a form of an embolization microcatheter. A distal outlet 128, which is provided at the catheter tip, is shaped or/and sized to allow passage therethrough of both the suspension fluid and the particles, while side openings 123 are configured to allow passage therethrough of the suspension fluid without the particles and to block passage therethrough of the particles, during delivery of the suspension 125 to the subject. In some embodiments, at least one of side openings 123 has a smallest cross sectional dimension (e.g., width, gap or diameter) equal to or less than about 1,000 microns, optionally particularly equal to or less than about 500 microns, optionally particularly equal to or less than about 100 microns, optionally particularly equal to or less than about 50 microns, optionally particularly equal to or less than about 30 microns.

Flow restraining mechanism 124 is located in proximity to distal outlet 128, distally to proximal outlet 126, and is configured to modify flow of the suspension 125, so as to decrease horizontal velocity component $V_3$ of the suspended particles 126 along a longitudinal axis X of the catheter 120. Flow restraining mechanism 124 includes at least one inwardly radial projection provided as a plurality of longitudinally spaced opened or/and closed ring elements 130, originating from inner boundary of catheter head lumen 131, configured to resist suspension 125 flowing thereacross. Each ring element 130 functions as an orifice in resisting (choking) the suspension portion that is pressurized to pass distally therethrough under a pressure $P_1$ that is developed in catheter head lumen 131 during injection (such as by activating a pressure source, such as pressure source 109 of FIG. 1, which may be in a form of a manual injector or a pump). The plurality of ring elements 130 contributes to a pressure difference between lumen pressure $P_1$ and surrounding (blood vessel) pressure $P_3$ such that $P_1$ is substantially greater than $P_3(P_1>P_3)$. As a result, and also due to a certain ratio between total opened cross section of side openings 123 and (total) opened cross section of distal outlet 128, the velocity $V_1$ of the suspension fluid volume dispersed through side openings 123 is substantially greater than horizontal velocity component $V_3$ of the suspended particles 126 (with remaining suspension fluid) along longitudinal axis X at the exit of distal outlet 128.

The total volume of suspension fluid that is dispersed through side openings 123 is equal to an “excess volume” 127R of suspension fluid (e.g., excess volume 102 of FIG. 1); and the particles with the remaining suspension fluid volume that passes (delivered) via distal outlet 128 is optionally a “concentrated suspension” 125C (e.g., concentrated suspension 112 of FIG. 1). In some embodiments, flow rate of the excess volume of the suspension fluid, via side openings 123, is optionally at least 0.5 cc/minute, optionally at least 1.5 cc/minute, or optionally 3 cc/minute. Flow rate of the concentrated suspension 125C, via distal outlet 128, is optionally about 1 cc/minute or less, or optionally about 0.5 cc/minute or less. In some embodiments, delivery horizontal velocity $V_3$ of the concentrated suspension 125C is approximately 50 cm/second or less, optionally particularly approximately 20 cm/second or less, optionally particularly approximately 5 cm/second or less.

FIG. 3 is a schematic sectional orthogonal view of an exemplary embodiment of a catheter 140 (formed by a catheter head 141 connected to a flexible tube 142) with a proximal outlet 146 (area) in a form of (or including) side openings 143, and a flow restraining mechanism 144. Catheter 140 is optionally similar or even identical in design or/and configuration to catheter 100, optionally similar to catheter 120 and differentiated only by orifices design or/and in resistance (coefficient) to flow, and is optionally in a form of an embolization microcatheter.

A distal outlet 148, which is provided at the catheter tip, is shaped or/and sized to allow passage therethrough of both suspension fluid and particles in a premade suspension, while side openings 143 are configured to allow passage therethrough of the suspension fluid and to block passage therethrough of the particles during delivery to the subject. In some embodiments, at least one of side openings 143 has a smallest cross sectional dimension (e.g., width, gap or diameter) equal to or less than about 1,000 microns, optionally particularly equal to or less than about 500 microns, optionally particularly equal to or less than about 100 microns, optionally particularly equal to or less than about 50 microns, optionally particularly equal to or less than about 30 microns.

Flow restraining mechanism 144 is located in proximity to distal outlet 148, distally to proximal outlet 146, and is configured to modify flow of the suspension, so as to decrease horizontal velocity component of the suspended particles along longitudinal axis of the catheter 140. Flow restraining mechanism 144 includes at least one inwardly radial projection provided as a plurality of longitudinally spaced concave orifices 150, originating from inner boundary of catheter head lumen 151, projected substantially inwardly and radially, and then bent substantially in a proximal direction towards proximal outlet 146. Each concave orifices 150 is configured to resist suspension flowing thereacross for resisting (choking) the suspension portion that is pressurized to pass distally therethrough under a pressure that is developed in catheter head lumen 151 during injection. The plurality of concave orifices 150 contributes to a positive pressure difference between lumen pressure and surrounding (blood vessel) pressure. As a result, and also due to a certain ratio between total opened cross section of side openings 143 and (total) opened cross section of distal outlet 148, the velocity of the suspension fluid volume dispersed through side openings 143 is substantially greater than horizontal velocity component of the suspended particles (with remaining suspension fluid) along longitudinal axis at the exit of distal outlet 148.

FIG. 4 is a schematic sectional orthogonal view of an exemplary embodiment of a catheter 160 (formed by a catheter head 161 connected to a flexible tube 162) with a proximal outlet 166 (area) in a form of (or including) side openings 163, and a flow restraining mechanism 164. Catheter 160 is optionally similar or even identical in design or/and configuration to catheter 100, optionally similar to catheter 120 and differentiated only by orifices design or/and in resistance (coefficient) to flow, and is optionally in a form of an embolization microcatheter.

A distal outlet 168, which is provided at the catheter tip, is shaped or/and sized to allow passage therethrough of both suspension fluid and particles in a premade suspension, while side openings 163 are configured to allow passage therethrough of the suspension fluid and to block passage therethrough of the particles during delivery to the subject. In some embodiments, at least one of side openings 163 has a smallest cross sectional dimension (e.g., width, gap or diameter) equal to or less than about 1,000 microns, optionally particularly equal to or less than about 500 microns, optionally particularly equal to or less than about 100 microns, optionally particularly equal to or less than about 50 microns, optionally particularly equal to or less than about 30 microns.

Flow restraining mechanism 164 is located in proximity to distal outlet 168, distally to proximal outlet 166, and is configured to modify flow of the suspension, so as to decrease horizontal velocity component of the suspended particles along longitudinal axis of the catheter 160. Flow restraining mechanism 164 includes a helix 170, extending axially in catheter head lumen 171 from proximally to proximal outlet 166 to adjacent distal outlet 168. Helix 170 is shaped and dimensioned so as to increase lateral velocity component of the suspended particles and to decrease longitudinal velocity component of the suspended particles, at the exit from distal outlet 168.

Figure 5A:
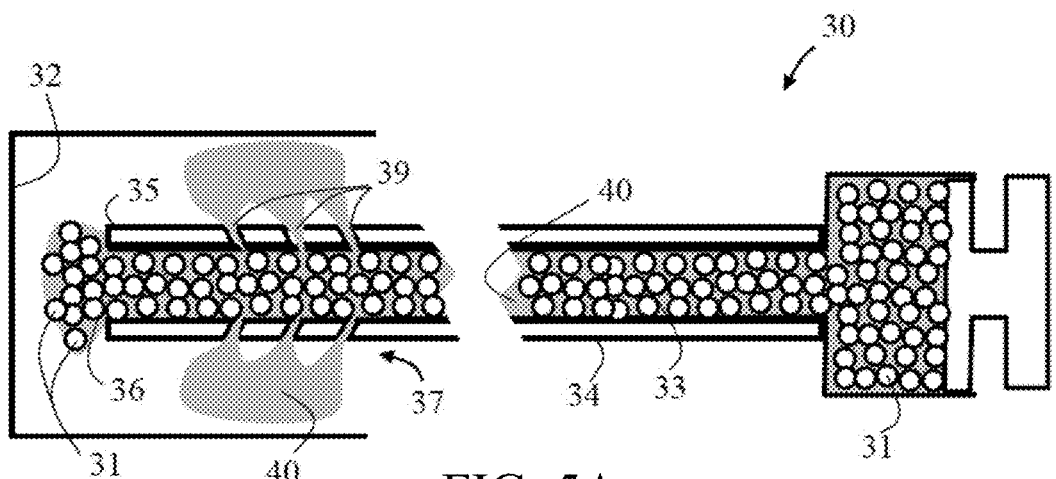
FIGS. 5A-5B are schematic sectional orthogonal views of exemplary embodiments of a microcatheter during delivery of a suspension before (FIG. 2A) and after (FIG. 2B) occurrence of a retrograded flow, in accordance with some embodiments of the invention.
Figure 5B:
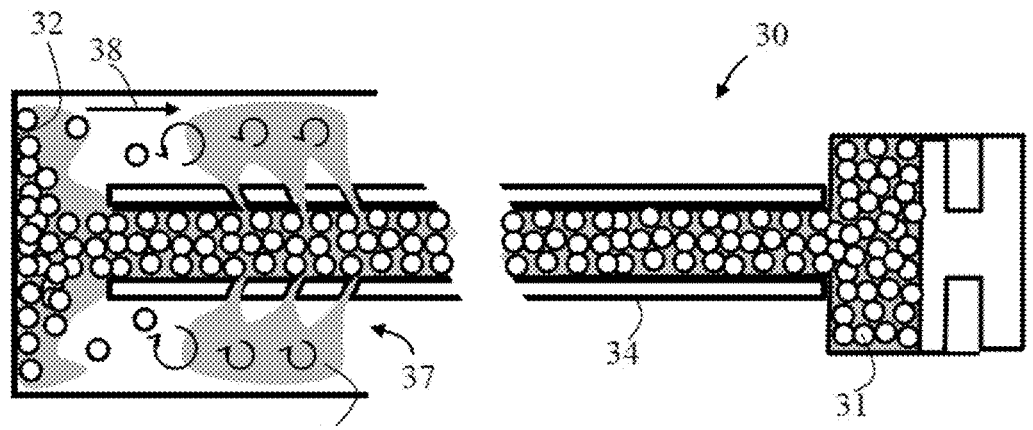

FIGS. 5A-5B are schematic sectional orthogonal views of exemplary embodiments of a catheter 30 during delivery of a suspension with an infusion agent 31 (in a form of beads or particles) before (FIG. 5A) and after (FIG. 5B) occurrence of a retrograded flow. Catheter 30 is optionally similar or even identical in design or/and configuration to catheter 100, and is optionally in a form of an embolization microcatheter.

Catheter 30 is optionally sized and configured for delivering infusion agent 31 in a small blood vessel towards a target bodily part 32. Catheter 30 includes a single lumen 33 surrounded by a tubular wall 34 having an outer diameter and opened at both ends. In some embodiments, tubular wall 34 is sized for unhindered insertion into a small blood vessel, such as a celiac or hepatic artery. In some embodiments, outer diameter of catheter 30 is equal to or less than about 2 mm, or equal to or less than about 1 mm. In some embodiments, catheter 30 has an external diameter equal to the diameter of a commercially available microcatheter, such as a 2.1 French catheter, or a 2.7 French catheter, or a 2.9 French catheter.

A proximal portion of tubular wall 34 is connectable to a pressure source and to a reservoir configured for containing an infusion suspension of an infusion agent (e.g., embolization material or/and contrast enhancing material) 31. Infusion agent 31 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). In exemplary embodiments, infusion agent 31 is of particulate form (e.g., non-spherical particles, or microspheres) having an average size (long dimension or diameter) in a range of between about 25 microns (μm) and about 1,500 microns (μm). In exemplary embodiments, infusion agent 31 has a compressibility in a range of between about 10% and about 40%. For example, polyvinyl alcohol (PVA) type infusion agent has a compressibility in a range of between about 20% and about 30%.

A distal portion of tubular wall ends with a tip 35, enclosing a distal outlet 36. Tubular wall 34 distal portion includes a proximal outlet 37 configured as a flow disruption section to disrupt passage of an incoming retrograded (in a general distal direction) flow 38 of the infusion agent around tubular wall 34, during continuous delivery of the infusion agent 31 from the reservoir to tip 35 and out through distal outlet 36. As shown in FIG. 2B, by dispersing infusion (suspension) fluid therethrough, proximal outlet 37 is configured to diminish, or block, incoming retrograded flow 38 of the infusion agent 31, for example, thereby increasing local pressure thereabout or/and creating local turbulence or vortex. In some embodiments, the turbulence or vortex is created by infusion fluid injected or otherwise expelled from the microcatheter, for example, wherein the infusion agent 31 is partially or fully filtered from the infusion fluid.

Proximal outlet 37 includes a plurality of openings 39 distributed around or/and along it, each opening is shaped or/and sized to effect passage therethrough of an infusion fluid (such as a viscous fluid) 40, and to block passage therethrough of the infusion agent 31. In exemplary embodiments, infusion fluid 40 includes a contrast enhancing material (agent), for example, diluted to a certain degree such as with saline. In some instances, the medical practitioner may mix together a viscous contrast enhancing material (such as a contrast enhancing material or agent) with embolization material (for example, including saline and embolization beads), for example, in a volumetric ratio of 50:50, thereby producing an infusion suspension of embolization beads and contrast enhancing material or agent diluted to a chosen degree. In an exemplary embodiment, the infusion suspension includes drug-eluting beads (DEB), chemotherapeutic material (e.g., doxorubicin) and contrast enhancing material. In exemplary embodiments, the contrast enhancing material (agent) may be, or include, any of various different types or kinds of contrast media, for example, Visipaque™ (iodixanol), or Omnipaque™ (iohexol), among many other suitable types and kinds of contrast media.

One or more opening 39 includes a pore having a cross sectional dimension less than minimal diameter of the infusion agent, for example, embolization material (e.g., bead diameter). Such cross sectional dimension is, for example, less than about 500 microns (μm), or, equal to or less than about 100 microns (μm), or, equal to or less than about 40 microns (μm). In exemplary embodiments, the cross section dimension is in a range of between about 20 microns (μm) and about 30 microns (μm), for example, about 28 microns (μm). For example, as shown, each pore is located at end of a channel being angled (wherein the angle is an exemplary range of between about 0 degrees and about 90 degrees) relative to a long axis of lumen 33 or/and relative to a radial axis thereof at a cross section adjacent thereto. In exemplary embodiments, at least two pores are angularly located in different directions such that a first stream of the infusion suspension in immediate vicinity of a first pore at least partially intersects a second stream of the infusion suspension in immediate vicinity of a second pore. Openings 39 or pores may be in any possible form, for example, with circular or rectangular cross section, or as a burst slit (i.e., opened only under chosen pressure or force), or a constantly opened slit. In such exemplary embodiments, the openings 39 or pores have a minimal cross sectional dimension being less than the minimal diameter of the infusion agent (e.g., embolization material, (for example, in the form of beads).

In some embodiments, lumen 33 is configured to deliver a suspension of infusion fluid 40 and infusion agent 31, for example, in a form of beads. In some embodiments, distal outlet 36 is shaped or/and sized to effect passage therethrough of the infusion suspension of infusion fluid 40 and the infusion agent (beads) 31, and at least one side opening 39 is shaped or/and sized to effect passage therethrough of infusion fluid 40, and to block passage therethrough of infusion agent (beads) 31, for example, if a cross sectional dimension of the pore in each opening is less than a minimal diameter of the infusion agent (beads).

In some embodiments, at least one side opening 39 is shaped or/and sized to effect passage therethrough of infusion fluid 40, and to block passage therethrough of infusion agent (beads) 31, during flow of the infusion suspension through distal outlet 36. In some other embodiments, at least one side opening 39 is shaped or/and sized to effect passage therethrough of infusion fluid 40, and to block passage therethrough of infusion agent (beads) 31, during conditions when the infusion suspension is blocked or interrupted from flowing through distal outlet 36.

In some embodiments, a total opened cross section of all openings 39 is equal to or greater than a smallest cross section of lumen 33 and distal outlet 36.

In some embodiments, infusion fluid 40 at normal body temperature has an average viscosity (expressed in terms of milliPascal second [mPa·s]) of at least about 0.8 mPa·s, or at least about 5 mPa·s, or at least about 10 mPa·s, or at least about 20 mPa·s. In exemplary embodiments, infusion fluid 40 is pre-heated, for example, to a temperature higher than about 37° C., before reaching tubular wall 34 distal portion in lumen 33. In exemplary embodiments, infusion fluid 40 includes, or is mixed with, another infusable fluid (e.g., glucose water), for example, also pre-heated with infusion fluid 40 or separately pre-heated.

In some embodiments, a farthest distal side opening 39 is located within a range of between about 0 mm and about 20 mm, or within a range of between about 0 mm and about 10 mm, or within a range of between about 0 mm and about 5 mm, proximally to distal outlet 36.

Figure 6:
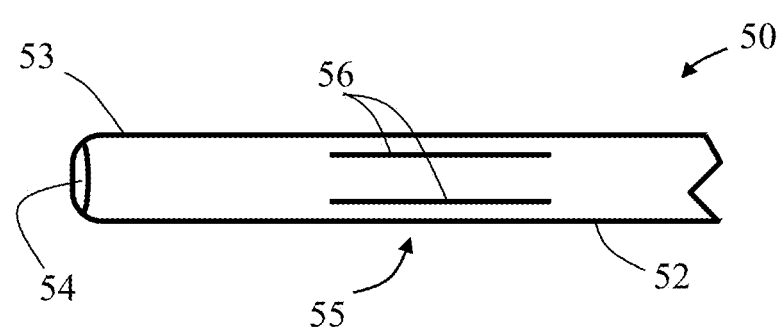
FIG. 6 is a schematic orthogonal view of an exemplary embodiment of a catheter distal portion having exemplary side openings in a form of slits, in accordance with some embodiments of the invention.

FIG. 6 is a schematic orthogonal view of an exemplary embodiment of catheter 50 including a proximal outlet 55 having side openings 56 in form of slits. Catheter 50 is optionally similar or even identical in design or/and configuration to catheter 100, and is optionally in a form of an embolization microcatheter. Catheter 50 is sized and configured for delivering infusion agent, for example, including embolization material (e.g., in a form of particles or beads) in a small blood vessel, towards a target bodily part. Catheter 50 includes a tubular wall 52 having a distal portion which ends with a tip 53, enclosing a distal outlet 54. Tubular wall 52 distal portion includes an infusion agent flow disruption section 55 configured to disrupt passage therethrough of an incoming retrograded flow of the infusion agent, for example, during continuous delivery of the infusion agent through distal outlet 54 by dispersing infusion (suspension) fluid therethrough, proximal outlet 55 is configured to block, or/and cause turbulence in, incoming retrograded flow of the infusion agent, thereby increasing local pressure thereabout.

Openings 56 are optionally distributed around or/and along it, each opening includes a slit with a gap having a cross sectional dimension (e.g., width) less than minimal diameter of the infusion agent. In exemplary embodiments, another cross sectional dimension of this gap (e.g., length) is substantially greater than the minimal diameter of the infusion agent. In some embodiments, each opening is shaped or/and sized to effect passage therethrough of an infusion fluid, and to block passage therethrough of the infusion agent.

In some embodiments, the wall portion surrounding proximal outlet 55 includes material being firmer than material of other sections of tubular wall 52 distal portion. In exemplary embodiments, it is made of a metallic material, a hard polymeric material, or a combination thereof. In exemplary embodiments, it is coated with a radiopaque material such as with hydrophilic coating. In exemplary embodiments, it is structured with a metal coil, for example, impregnated with solid structure or/and attached to a layer of solid structure.

FIGS. 7A-7B are schematic partial sectional orthogonal views of exemplary embodiments of a portion of an infusion agent flow disruption section 61 (in exemplary catheter 60) that includes a valve mechanism 62 over a proximal outlet, before (FIG. 7A) and after (FIG. 7B) actuation thereof. Catheter 60 is optionally similar or even identical in design or/and configuration to catheter 100, and is optionally in a form of an embolization microcatheter sized and configured for delivering infusion agent (e.g., embolization material or/and contrast enhancing material) 63 (e.g., in the form of particles) in a blood vessel towards a target bodily part. Catheter 60 includes a lumen 64 surrounded by a tubular wall 65 having an outer diameter and opened at both ends. In some embodiments, tubular wall 65 is sized for unhindered insertion into a small blood vessel, such as a celiac or hepatic artery. In some embodiments, outer diameter of catheter 60 is equal to or less than about 4 mm, or, equal to or less than about 2 mm. In some embodiments, catheter 60 has an external diameter equal to the diameter of a commercially available microcatheter, such as a 2.1 French catheter, a 2.7 French catheter, or a 2.9 French catheter.

Infusion agent 63 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). In exemplary embodiments, infusion agent 63 is of particulate form (e.g., non-spherical particles, or microspheres) having an average size (long dimension or diameter) in a range of between about 25 microns (μm) and about 1,500 microns (μ). In exemplary embodiments, infusion agent 63 has a compressibility in a range of between about 10% and about 40%. For example, polyvinyl alcohol (PVA) type infusion agent has a compressibility in a range of between about 20% and about 30%.

Infusion agent flow disruption section 61 is configured to disrupt passage of an incoming retrograded flow 69 of the infusion agent around outer periphery of tubular wall 65 distal end adjacent thereto, during continuous delivery of infusion agent 63 through distal outlet of microcatheter 60. Flow disruption section 61 is configured to diminish, block, or/and cause turbulence or vortex in, incoming retrograded flow 69 of the infusion agent, optionally increasing local pressure thereabout.

Proximal outlet in flow disruption section 61 includes a plurality of side openings 66 distributed around or/and along it, each opening is shaped or/and sized to allow passage therethrough of an infusion fluid 67, and to block passage therethrough of the infusion agent 63.

Infusion (suspension) fluid 67, in exemplary embodiments, includes a contrast enhancing agent, for example, diluted to a certain degree such as by saline. In some instances, the medical practitioner may mix together a viscous contrast enhancing media with infusion agent, for example, embolization material including saline and embolization beads, for example, in a volumetric ratio of 50:50, thereby producing a viscous fluidic infusion suspension of embolization beads and contrast enhancing media diluted to a chosen degree. In exemplary embodiments, the contrast enhancing material (agent) may be, or include, any of various different types or kinds of contrast media, for example, Visipaque™ (iodixanol), or Omnipaque™ (iohexol), among many other suitable types and kinds of contrast media.

One or more opening 66 includes a pore having a cross sectional dimension less than minimal diameter of the infusion agent embolization material (e.g., bead diameter). Such cross sectional dimension is, for example, less than about 500 microns (μm), or, equal to or less than about 100 microns (μm), or, equal to or less than about 40 microns (μm). In exemplary embodiments, the cross section dimension is in a range of between about 20 microns (μm) and about 30 microns (μm), for example, about 28 microns (μm). For example, as shown, each pore is located at end of a channel being angled relative to a long axis of lumen 64 or/and relative to a radial axis thereof at a cross section adjacent thereto. In exemplary embodiments, at least two pores are angularly located in different directions such that a first stream of the infusion suspension in immediate vicinity of a first pore at least partially intersects a second stream of the infusion suspension in immediate vicinity of a second pore.

In some embodiments, lumen 64 is configured to deliver a suspension of infusion fluid 67 and infusion agent 63 (e.g., in a form of particles/beads). In some embodiments, a distal outlet of catheter 60 is shaped or/and sized to allow passage therethrough of the suspension of infusion fluid 67 and the beads 63, and each of the side opening 66 is shaped or/and sized to allow passage therethrough of infusion fluid 67, and to block passage therethrough of most or all beads 63, for example if at least one cross sectional dimension (e.g., length, width, diameter) of the pore each opening is less than a minimal diameter of the beads.

In some embodiments, each side opening 66 is shaped or/and sized to allow passage therethrough of infusion fluid 67, and to block passage therethrough of beads 63, during flow of the infusion suspension through the distal outlet. In some other embodiments, each side opening 66 is shaped or/and sized to allow passage therethrough of infusion fluid 67, and to block passage therethrough of beads 63, during conditions when the infusion suspension is blocked or interrupted from flowing through the distal outlet.

In some embodiments, a total opened cross section of all side openings 66 is equal to or greater than a smallest cross section of lumen 64 and the distal outlet.

In some embodiments, infusion fluid 67 at normal body temperature has an average viscosity of at least about 0.8 mPa·s, or at least about 5 mPa·s, or at least about 10 mPa·s, or at least about 20 mPa·s. In exemplary embodiments, infusion fluid 67 is pre-heated, for example, to a temperature higher than about 37° C., before reaching tubular wall 65 distal portion in lumen 64.

In some embodiments, a farthest distal side opening 66 is located within a range of between about 0 mm and about 20 mm, or within a range of between about 0 mm and about 10 mm, or within a range of between about 0 mm and about 5 mm, proximally to the distal outlet.

Valve mechanism 62 is configured to cover side openings 66 when pressure inside tubular wall 65 distal portion is less than a predetermined pressure, and to uncover side openings 66 when pressure inside the tubular wall distal portion is greater than the predetermined pressure. Internal pressure may be built using an orifice or a narrowing (as shown in FIGS. 2A and 2B, for example) at the distal outlet. In some embodiments, valve mechanism 62 includes a cover 68 configured to cover the plurality of side openings 66 and to prevent passage therethrough of fluids, and configured to uncover the plurality of side openings 66 when tubular wall 65 section is immersed in a proximally flowing fluid, such as for example, when it is provided in the small blood vessel when retrograded flow occurs. The tubular wall section 65 may include a space between the plurality of side openings 66 and cover 68, which is sized to accumulate a predetermined maximal volume of infusion fluid 67 absent of beads 63. Such predetermined maximal volume may be in a range of between about 0 ml and about 1 ml. In exemplary embodiments, the predetermined maximal volume is at least about 1 ml, or at least about 5 ml, or at least about 10 ml.

Cover 68 may be fabricated from metal, for example, a super-elastic metal alloy (e.g., nitinol or stainless steel), or from a polymer (e.g., PTFE, ePTFE, polyester, FEP, urethane, Pebax, or Pellethane) for example, rigid or semi-rigid.

In some embodiments, cover 68 may increase the overall microcatheter diameter by an amount between about 0.5 mm and about 1 mm, for example, about 0.8 mm, when cover 68 is in a closed position. In some embodiments, cover 68 may increase the overall microcatheter diameter by an amount between about 1 mm and about 10 mm, for example, by about 5 mm, when cover 68 is in an opened position. In exemplary embodiments, cover 68 has a length in a range of between about 1 mm and about 5 mm. In exemplary embodiments, cover 68 has a thickness in a range of between about 20 microns and about 500 microns. In exemplary embodiments, cover 68 is attached to tubular wall 65 via at least one of: laser cut hinges, gluing, melting, and heat shrinking of an outer layer.

Reference is now made to FIG. 8, which is a schematic sectional orthogonal view of an exemplary embodiment of a catheter 70. Catheter 70 is optionally similar or even identical in design or/and configuration to catheter 100, and is optionally in a form of an embolization microcatheter. Catheter 70 includes a flexible tube 71 connected to a proximal end 72 of a tip 73. Tip 73 includes a rigid tubular wall 74, and encloses a distal outlet 75 opened to a tip lumen 76 extending along tubular wall 74. Catheter 70 includes a proximal outlet as a plurality of side openings 77 distributed around and along a section of tubular wall 74.

Flexible tube 71 is connected to proximal end 72 of tip 73 such that tip lumen 76 integrates with a lumen 79 provided along flexible tube 71, thus forming a catheter lumen 80. Catheter lumen 80 is configured to deliver a suspension of a suspension fluid and particulate embolization material, wherein distal outlet 75 is shaped or/and sized to allow passage therethrough of the suspension fluid and particles, and each side opening 77 is shaped or/and sized to allow passage therethrough of the suspension fluid, and to block passage therethrough of the particles. In some embodiments, a total opened cross section of the plurality of side openings 77 is equal to or greater than a smallest cross section of microcatheter lumen 80 and distal outlet 75.

At least one side opening 77 may include a slit with a gap having a cross sectional dimension less than a minimal diameter of the beads. Optionally, additionally or alternatively, and as shown, at least one side opening 77 includes a pore having a cross sectional dimension less than a minimal diameter of the beads. Optionally, each pore is located at end of a channel being angled relative to a long axis of tip lumen 76 or/and relative to a radial axis thereof at a cross section adjacent thereto.

A smallest cross sectional dimension of the side openings 77 may be equal to or less than 100 microns. In some embodiments, side openings 77 are constructed using a procedure of, or including, laser cutting, laser drilling, etching, EDM, or a combination thereof. Tubular wall 74 may be made of a metallic material, a hard polymeric material, or a combination thereof, and tube 71 is made of a flexible polymeric material.

Figure 9:
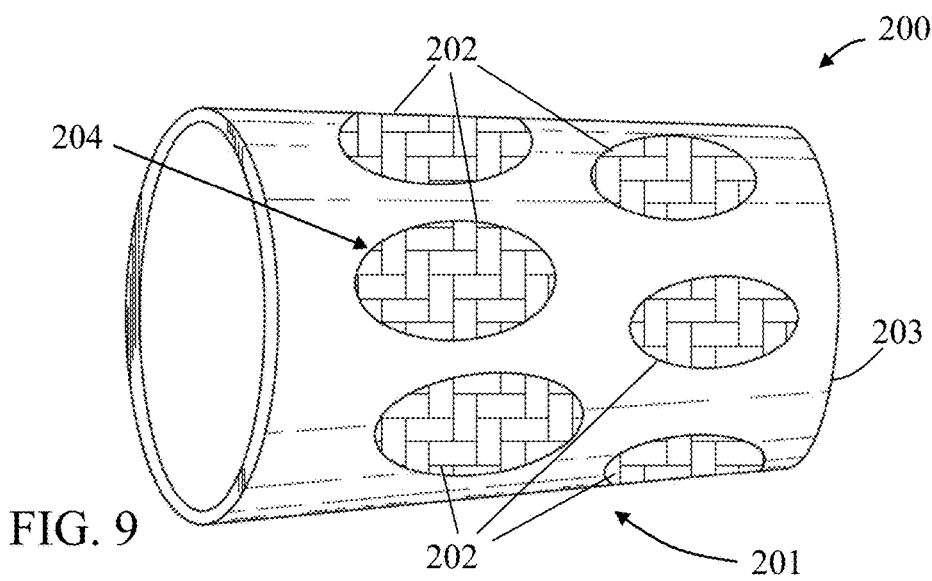
FIG. 9 is a schematic isometric view of an exemplary embodiment of catheter portion with meshed side openings, in accordance with some embodiments of the invention.

FIG. 9 is a schematic isometric view of an exemplary embodiment of a catheter portion 200 with a proximal outlet 201 incorporating meshed side openings 202. Catheter portion 200 is optionally part of a catheter similar or even identical in design or/and configuration to catheter 100 or/and to catheter 120, and is optionally in a form of an embolization microcatheter. In this exemplary configuration, catheter portion 200 is made of tubular wall 203, optionally of polymeric material, which covers or embeds sleeve made of textile material, optionally woven or-non-woven, optionally of intertwined fiber, thereby creating a mesh pattern 204 with mesh openings. These mesh openings are sized for allowing suspension fluid flowing therethrough but to block particles, of optionally 30 microns or more in diameter, from passing therethrough. Each of the side openings 202 made in tubular wall 203 reveals an area of sleeve mesh pattern.

Figure 10:
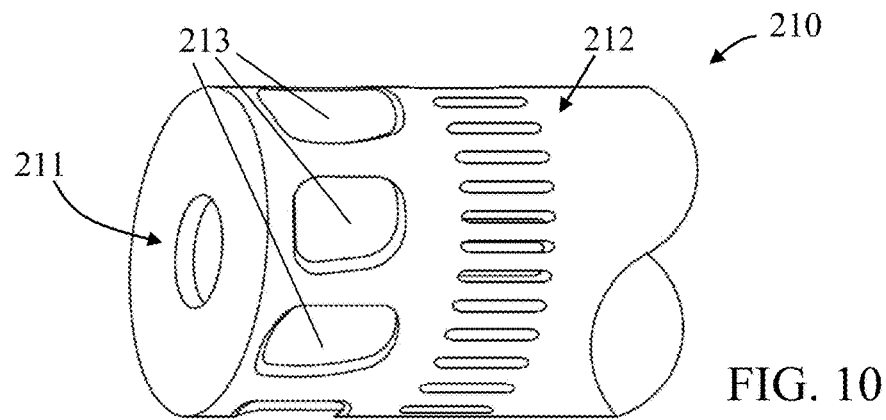
FIG. 10 is a schematic isometric view of an exemplary embodiment of a catheter head portion having silencer-mode configuration, in accordance with some embodiments of the invention.

FIG. 10 is a schematic isometric view of an exemplary embodiment of a catheter head portion 210 including a distal outlet 211 in a form of orifice, for delivering suspension of particles in a suspension fluid in a blood vessel towards a target location. Catheter head portion 210 also includes a proximal outlet 212 in a form of slits sized to allow suspension fluid passing therethrough but to block particles, of optionally 30 microns or more in diameter, from passing therethrough. In an intermediate section, between distal outlet 211 and proximal outlet 212, a plurality of large openings 213 is distributed around circumference of the catheter head portion 210, each of the large opening 213 is sized for passing both particles and suspension fluid therethrough, in a lateral direction relative to catheter longitudinal axis, thereby facilitating reduction in longitudinal velocity component of the particles deliverable through distal outlet 211. Catheter head portion 210 is optionally part of a catheter similar or even identical in design or/and configuration to catheter 100 or/and to catheter 120, and is optionally in a form of an embolization microcatheter.

Figure 11:
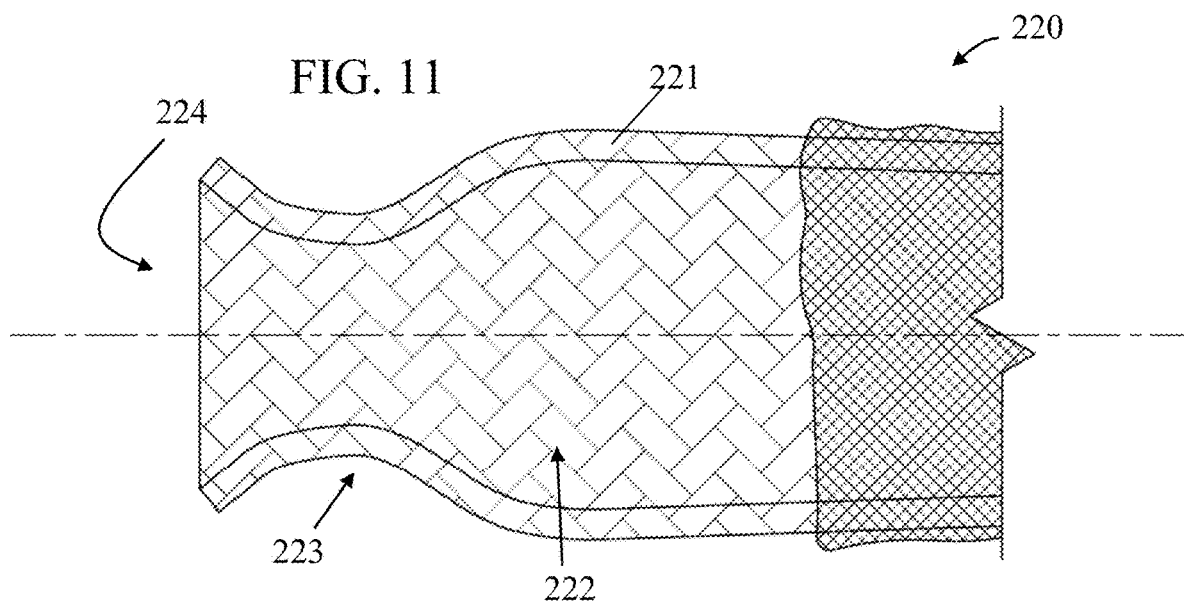
FIG. 11 is a schematic orthogonal view of an exemplary embodiment of braided portion of catheter head incorporating a converging-diverging segment, in accordance with some embodiments of the invention.

FIG. 11 is a schematic orthogonal view of an exemplary embodiment of a catheter head portion 220 including a tubular wall portion 221, forming a mesh pattern 222, and incorporating a converging-diverging segment 223. Mesh pattern 222 has mesh openings sized for allowing suspension fluid flowing therethrough but to block particles, of optionally 30 microns or more in diameter, from passing therethrough. Converging-diverging segment 223 is opened at a distal outlet 224 and is shaped and configured to suppress suspension fluid flowing therethrough, thereby facilitating reduction in longitudinal velocity component of the particles deliverable through distal outlet 224. Catheter head portion 220 is optionally part of a catheter similar or even identical in design or/and configuration to catheter 100 or/and to catheter 120, and is optionally in a form of an embolization microcatheter.

Figure 12A:
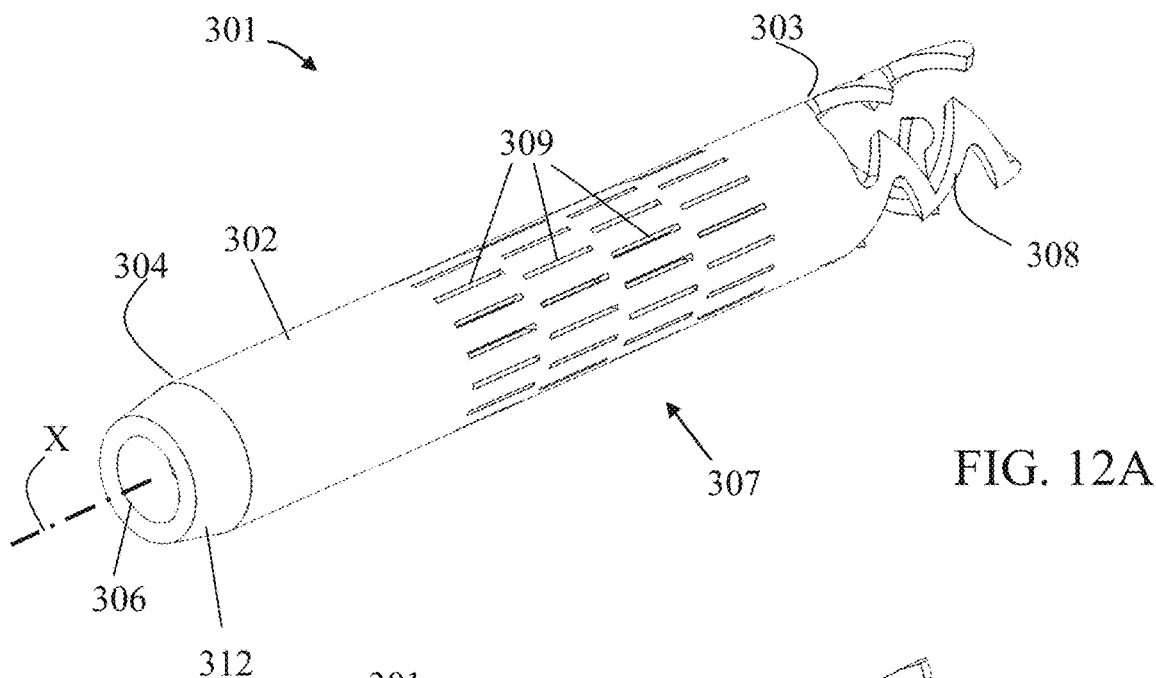
FIGS. 12A-12C illustrate an isometric view of a catheter head (FIG. 12A), a sectional isometric view of the catheter head (FIG. 12B), and a sectional orthogonal view of the catheter head (FIG. 12C), in accordance with some embodiments of the invention.
Figure 12B:
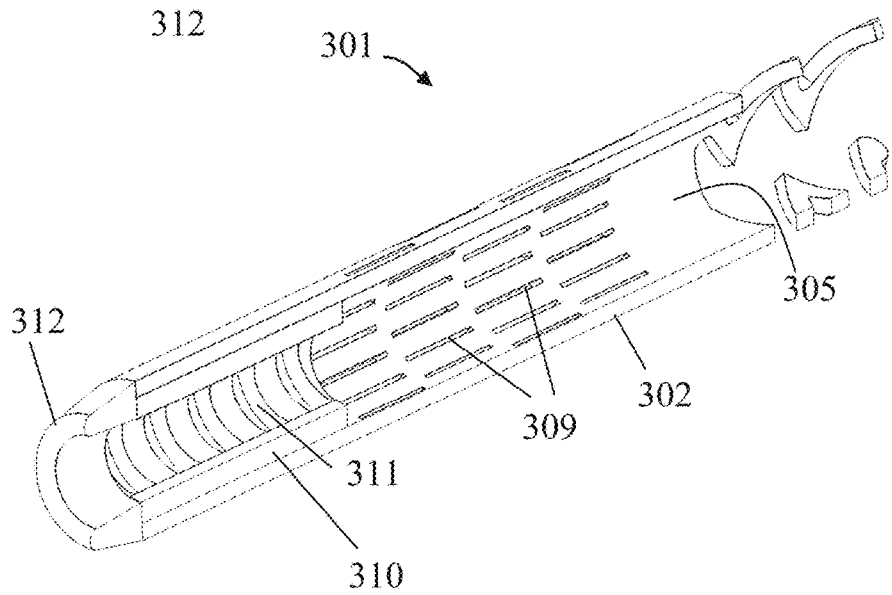
Figure 12C:
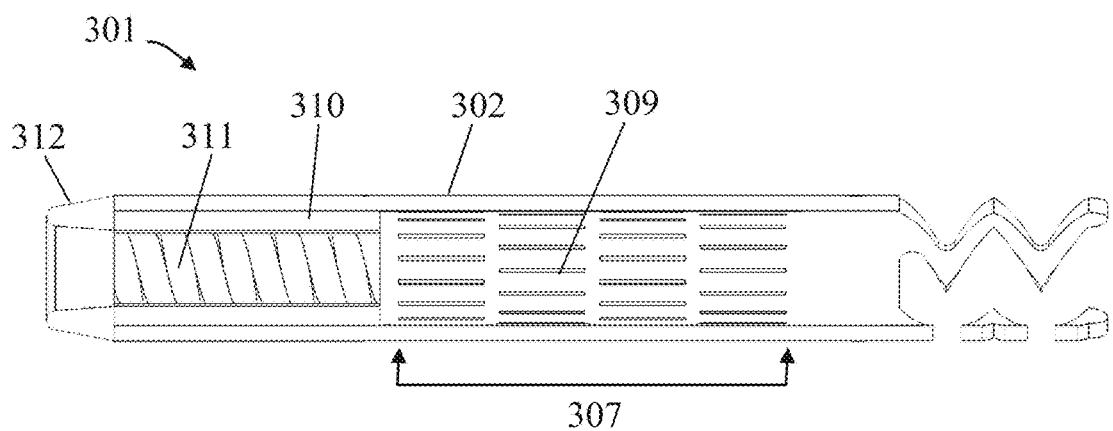

Reference is now made to FIGS. 12A-12C which illustrate an isometric view of a catheter head 301 (FIG. 12A), a sectional isometric view of the catheter head 301 (FIG. 12B), and a sectional orthogonal view of the catheter head 301 (FIG. 12C). Catheter head 301 is optionally part of a catheter similar or even identical in design or/and configuration to catheter 100 or/and to catheter 120, and is optionally in a form of an embolization microcatheter.

Catheter head 301 includes a tubular head wall 302 which includes a proximal head end 303 and a distal head end 304. Tubular head wall 302 encloses a head lumen 305 extending along head wall 302 and opened to a distal outlet 306 at distal head end 304 and is opened also to a proximal outlet 307 proximally to distal outlet 306. Catheter head 301 is connectable to a flexible tube with proximal head end 303, using connecting extensions 308, for integrating into a catheter (such as catheter 100). Connection is optionally done by melting distal portion of the of the flexible tube and allowing re-hardening over connecting extensions 308, or/and using adhesive.

Distal outlet 306 is shaped or/and sized to allow passage therethrough of the suspension fluid and the particles, and proximal outlet 307 is configured to allow passage therethrough of the suspension fluid and to block passage therethrough of the particles. Proximal outlet 307 includes a plurality of longitudinal slits 309 extending with a length thereof substantially parallel to a longitudinal axis X of the catheter, the slits 309 are distributed as staggered rows around and along a section of catheter head 301. Each slit includes a gap having a width smaller than a minimal diameter of the prescribed particles (e.g., 40 microns or more, in diameter), thereby facilitating particles blocking.

Catheter head 301 includes a flow restraining mechanism 310 (provided in this example as an insert connected in head lumen 305) including a helix 311 in approximation to distal outlet 306. Flow restraining mechanism 310 is configured to modify flow of the suspension so as to decrease horizontal velocity component of the particles along longitudinal axis X of catheter 300. Helix 311 is shaped and dimensioned to increase lateral velocity component of the particles and to decrease longitudinal velocity component of the particles, when the flow of suspension travels thereacross.

In some embodiments, outer diameter tubular head wall 302 is equal to or less than about 4 mm, optionally equal to or less than about 1 mm, or/and is configured for insertion into a small blood vessel originating from a celiac or hepatic artery.

In some embodiments, head wall 302 is made of a metallic material. In some such embodiments, the slits 309 are formed by one of laser cutting, laser drilling, etching, EDM, or any combination thereof. In some other embodiments, head wall 302 is made of a polymeric material, and in some such embodiments, the slits 309 are formed by one of femtolaser and skiving.

Catheter wall 301 includes an atraumatic tip 312 connected to distal head end 304 of tubular wall 302 and extends distal outlet 306. Atraumatic tip 312 is optionally made of soft polymer and is intended for diminishing or preventing harm to surrounding tissue.

Figure 13A:
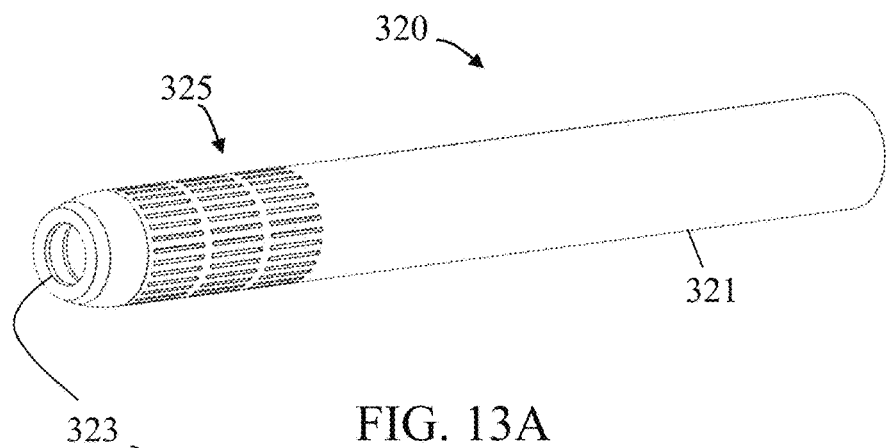
FIGS. 13A and 13B illustrate a full isometric view and a sectional orthogonal view, respectively, of an exemplary embodiment of a catheter distal portion having a plurality of longitudinal slits and a converging atraumatic tip, in accordance with some embodiments of the invention.
Figure 13B:
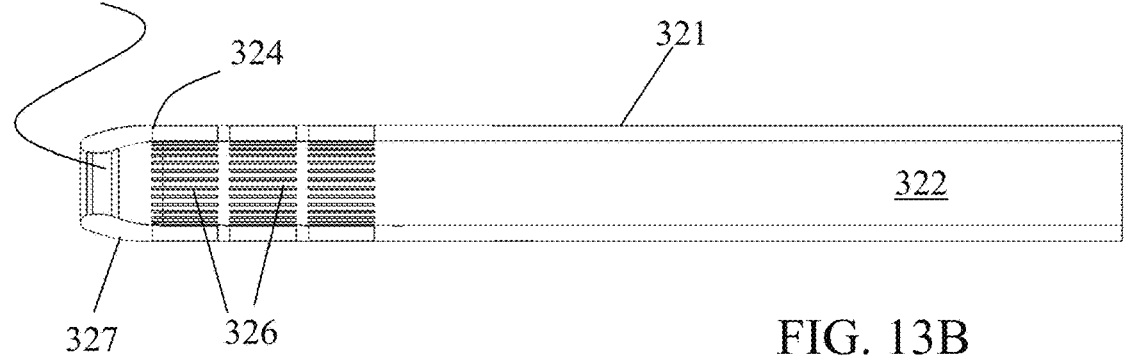

FIGS. 13A-13B illustrate a full isometric view and a sectional orthogonal view, respectively, of an exemplary embodiment of a distal portion of a catheter 320, which is optionally similar or even identical in design or/and configuration to catheter 100 or/and to catheter 120, and is optionally in a form of an embolization microcatheter.

Catheter 320 includes tubular wall 321 which includes lumen 322 opened to a distal outlet 323 at a distal wall end 324, and to a proximal outlet 325 located proximally to distal outlet 323. The catheter is configured to deliver the suspension via lumen 322 to distal outlet 323, therefore distal outlet 323 is shaped or/and sized to allow passage therethrough of the suspension fluid and the particles.

Tubular wall 321 outer diameter is optionally equal to or less than about 4 mm. The catheter is optionally configured as an embolization microcatheter. In some such embodiments, tubular wall 321 outer diameter is optionally equal to or less than about 1 mm or/and configured for insertion into a small blood vessel, such as one originating from a celiac or hepatic artery. In some embodiments, catheter 320 has an external diameter equal to the diameter of a commercially available microcatheter, such as a 2.1 French (0.7 mm) catheter, or a 2.7 French (0.9 mm) catheter, or a 2.9 French (0.97 mm) catheter.

In some embodiments, proximal outlet 325 is configured to allow passage therethrough of the suspension fluid and to block passage therethrough of the particles. Proximal outlet 325 includes a plurality of longitudinal slits 326 extending with a length thereof substantially parallel to a longitudinal axis of the catheter, the slits 326 are evenly spaced around and along a section of catheter 320 distal portion. Each slit includes a gap having a width smaller than a minimal diameter of the prescribed particles (e.g., 40 microns or more, in diameter), thereby facilitating particles blocking.

Tubular wall 321 includes an atraumatic tip 327 connected to distal wall end 324 of and extends distal outlet 323. Atraumatic tip 327 has a tubular shape converging in a distal direction, optionally configured as a flow restraining mechanism to modify flow of the suspension so as to decrease horizontal velocity component of the particles along the longitudinal axis of catheter 320. Atraumatic tip 327 is optionally made of soft polymer and is intended for diminishing or preventing harm to surrounding tissue.

Figure 14A:
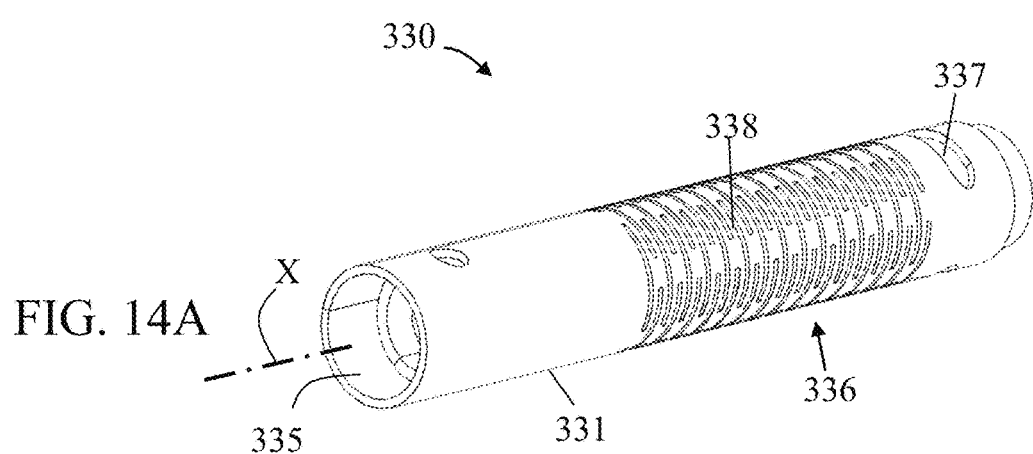
FIGS. 14A and 14B illustrate a full isometric view and a sectional isometric view, respectively, of an exemplary embodiment of a catheter head having a plurality of staggered lines of circumferential slits and a plurality of inwardly radial projections, in accordance with some embodiments of the invention.
Figure 14B:
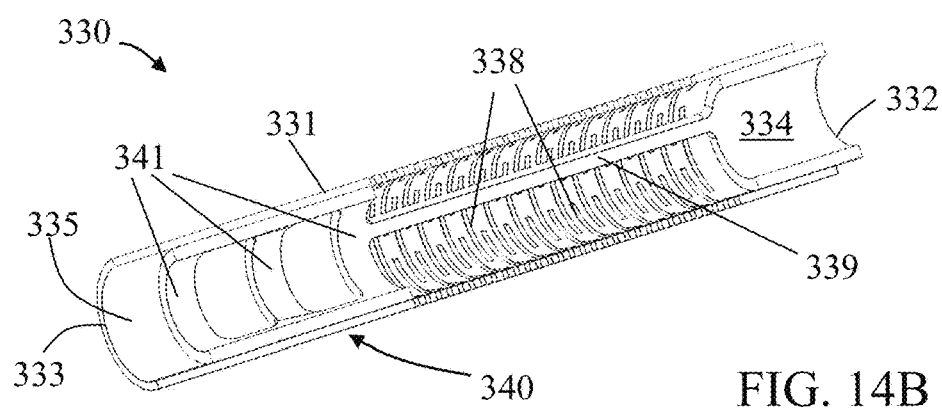

FIGS. 14A-14B illustrate a full isometric view and a sectional isometric view, respectively, of an exemplary embodiment of a catheter head 330 which is optionally part of a catheter similar or even identical in design or/and configuration to catheter 100 or/and to catheter 120, and is optionally in a form of an embolization microcatheter.

Catheter head 330 includes a tubular head wall 331 which includes a proximal head end 332 and a distal head end 333. Tubular head wall 331 encloses a head lumen 334 extending along head wall 331 and opened to a distal outlet 335 at distal head end 333 and is opened also to a proximal outlet 336 proximally to distal outlet 335. Catheter head 330 is connectable to a flexible tube with proximal head end 332, using connection cavities 337, for integrating into a catheter (such as catheter 100). Connection is optionally done by melting distal portion of the of the flexible tube and allowing re-hardening over connection cavities 337, or/and using adhesive.

Distal outlet 335 is shaped or/and sized to allow passage therethrough of the suspension fluid and the particles, and proximal outlet 336 is configured to allow passage therethrough of the suspension fluid and to block passage therethrough of the particles. Proximal outlet 336 includes a plurality of staggered lines of circumferential slits 338 extending with a length thereof substantially vertically to a longitudinal axis X of the catheter. Each slit includes a gap having a width smaller than a minimal diameter of the prescribed particles (e.g., 40 microns or more, in diameter), thereby facilitating particles blocking.

In some embodiments, outer diameter tubular head wall 331 is equal to or less than about 4 mm, optionally equal to or less than about 1 mm, or/and is configured for insertion into a small blood vessel originating from a celiac or hepatic artery.

In some embodiments, head wall 331 is made of a metallic material. In some such embodiments, the slits 338 are formed by one of laser cutting, laser drilling, etching, EDM, or any combination thereof. In some other embodiments, head wall 331 is made of a polymeric material, and in some such embodiments, the slits 338 are formed by one of femtolaser and skiving.

Catheter head 330 includes a catheter length limiting rod-like element 339 extending substantially parallel to longitudinal axis X across proximal outlet 336 (across all slits 338), thereby resisting or/and preventing elongation of the catheter about proximal outlet 336.

Catheter head 330 includes a flow restraining mechanism 340 configured as inwardly radial projections 341. In this example, the radial projections 341 are extensions of rod-like element 339 in form of closed rings curved in conformity to inner boundaries of head lumen 334 (provided in this example as an insert connected in head lumen 334). Flow restraining mechanism 340 is configured to dissipate kinetic energy thereby to decrease horizontal velocity component of the particles along longitudinal axis X of catheter head 330.

Figure 15:
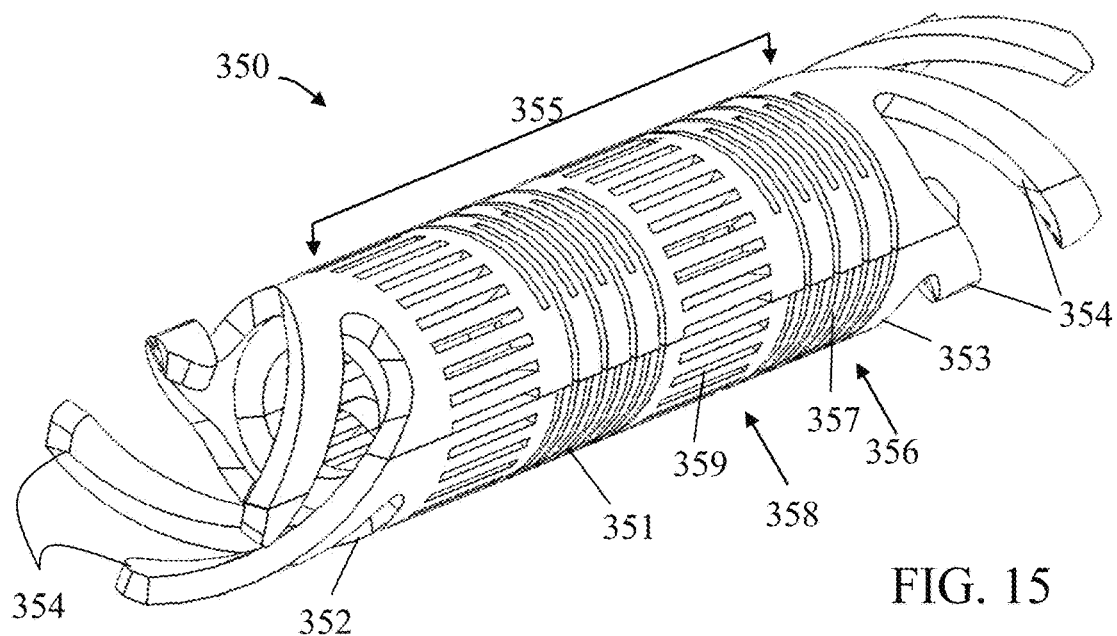
FIG. 15 is an isometric view of an exemplary embodiment of a microcatheter head component having circumferential slits and longitudinal slits, in accordance with some embodiments of the invention.

FIG. 15 is an isometric view of an exemplary embodiment of a catheter head component 350 including a tubular head wall 351 with a distal wall end 352 and a proximal wall end 353. Each of distal wall end 352 and proximal wall end 353 includes a number of helical extensions 354 connectable to other components for forming a catheter (such as catheter 100). Distal wall end 352 is connectable to an atraumatic tip (such as atraumatic tip 327 of FIG. 13) and proximal wall end 353 is connectable to a flexible tube (such as flexible tube 71 of FIG. 8). Head wall 351 includes a proximal port 355 along most length thereof, which is divided into consecutive tubular segments, each two adjacent segment has a different pattern of slits, including a first segment 356 having circumferential slits 357 and a second segment 358 having longitudinal slits 359.

Figure 16A:
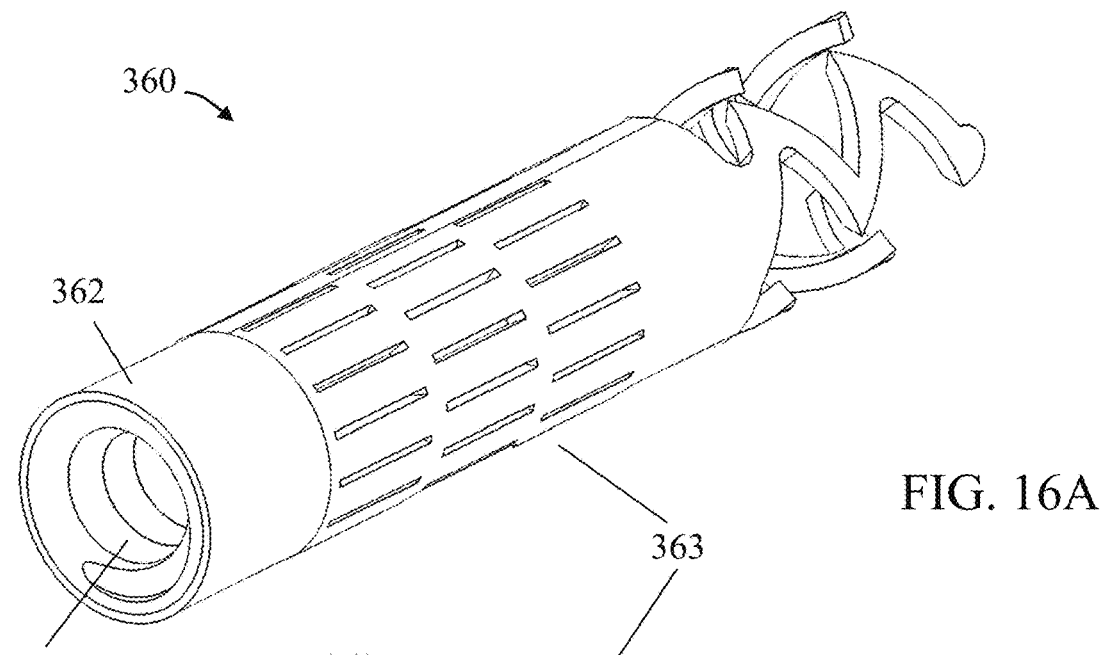
FIGS. 16A and 16B illustrate a full isometric view and a sectional orthogonal view, respectively, of an exemplary embodiment of a catheter head having a plurality of staggered rows of longitudinal slits and a helix, in accordance with some embodiments of the invention.
Figure 16B:
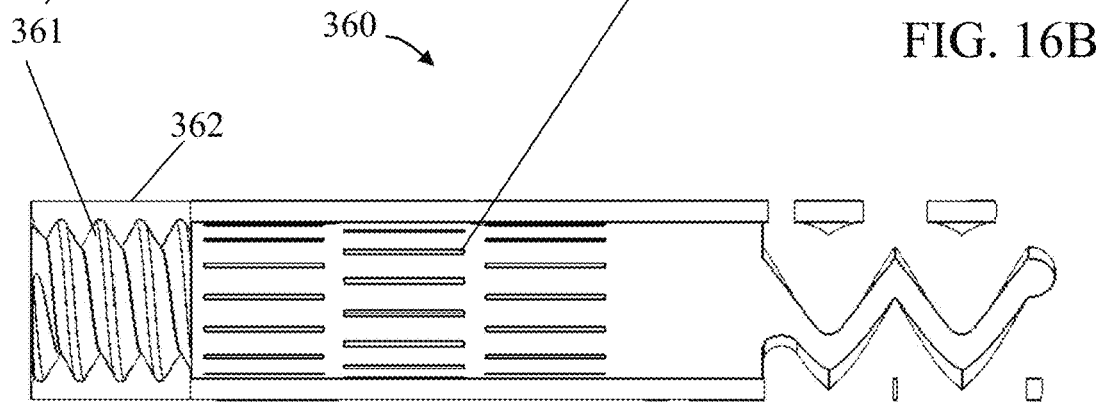

FIGS. 16A-16B illustrate a full isometric view and a sectional orthogonal view, respectively, of an exemplary embodiment of a catheter head 360, which is optionally similar or even identical in design or/and configuration to catheter 100, and is optionally in a form of an embolization microcatheter. Optionally, catheter head 360 is a variation of catheter head 301 of FIG. 12, differentiated only with that it includes a helix 361 being embedded/integral in atraumatic tip 362. Similar to proximal outlet 307 of catheter head 301, catheter head 360 includes a plurality of longitudinal slits 363 extending with a length thereof substantially parallel to a longitudinal axis of the catheter, the slits 363 are distributed as staggered rows around and along a section of catheter head 301. Each slit 363 includes a gap having a width smaller than a minimal diameter of the prescribed particles (e.g., 40 microns or more, in diameter), thereby facilitating particles blocking.

Figure 17A:
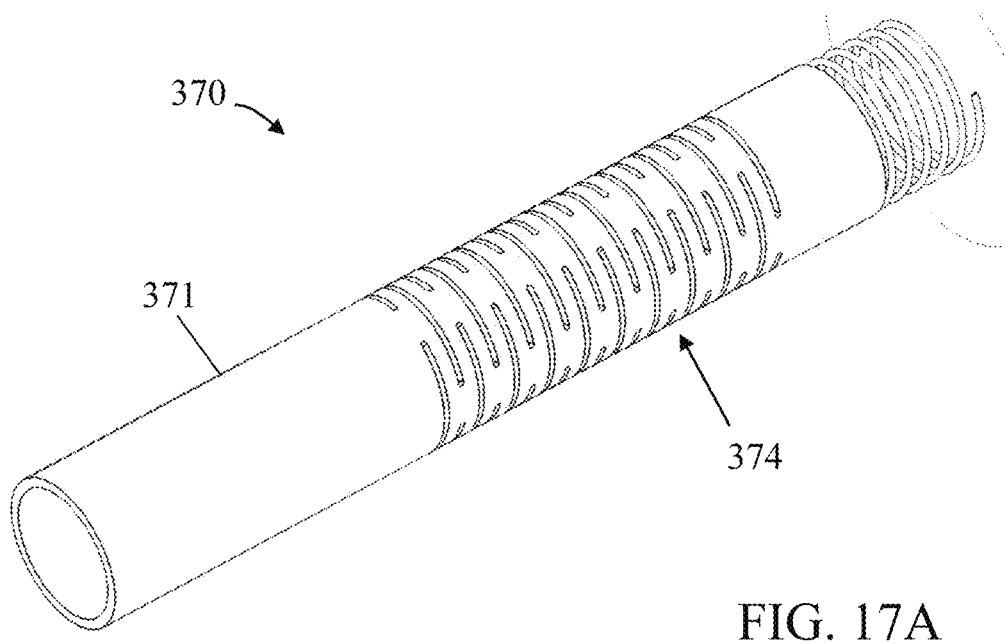
FIGS. 17A and 17B illustrate a full isometric view and a sectional isometric view, respectively, of an exemplary embodiment of a catheter distal portion made of reinforced polymer and having a plurality of staggered lines of circumferential slits and a plurality of inwardly radial projections, in accordance with some embodiments of the invention.
Figure 17B:
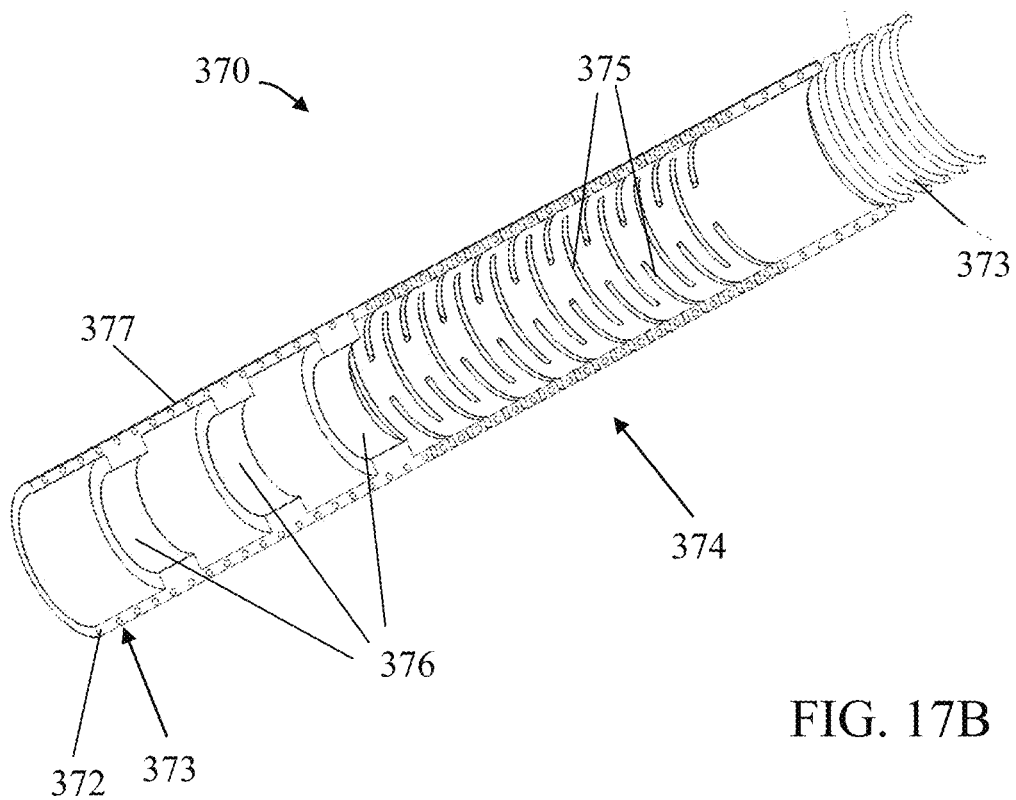
Figure 18A:
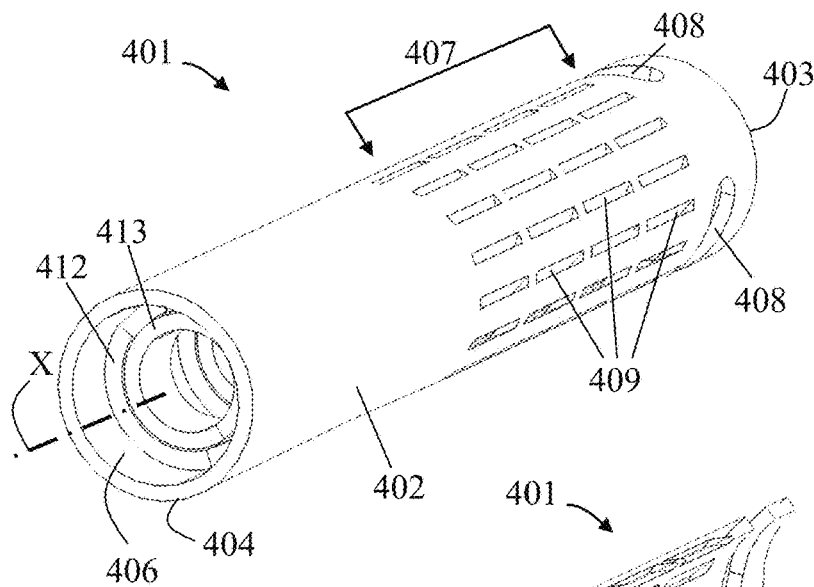
FIGS. 18A-18D illustrate an isometric view of an exemplary embodiment of a catheter head having a plurality of tangential longitudinal slits and a plurality of convex orifices (FIG. 18A), a sectional isometric view of the catheter head (FIG. 18B), a cross-sectional isometric view of the catheter head (FIG. 18C), and a sectional orthogonal view of the catheter head (FIG. 12D), in accordance with some embodiments of the invention.
Figure 18B:
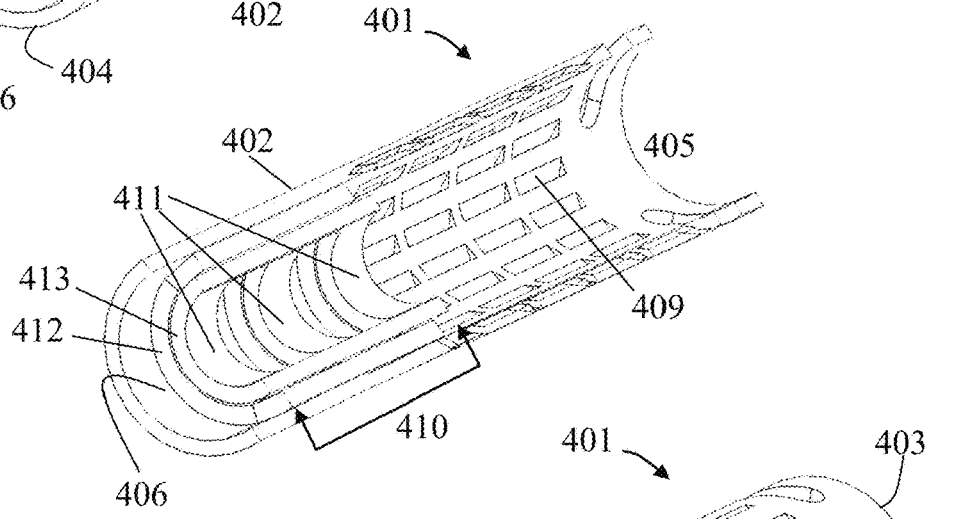
Figure 18C:
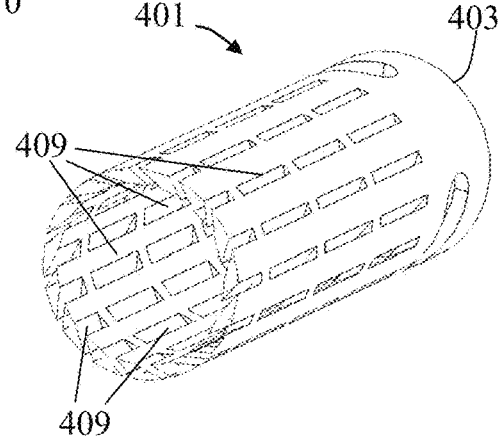
Figure 18D:
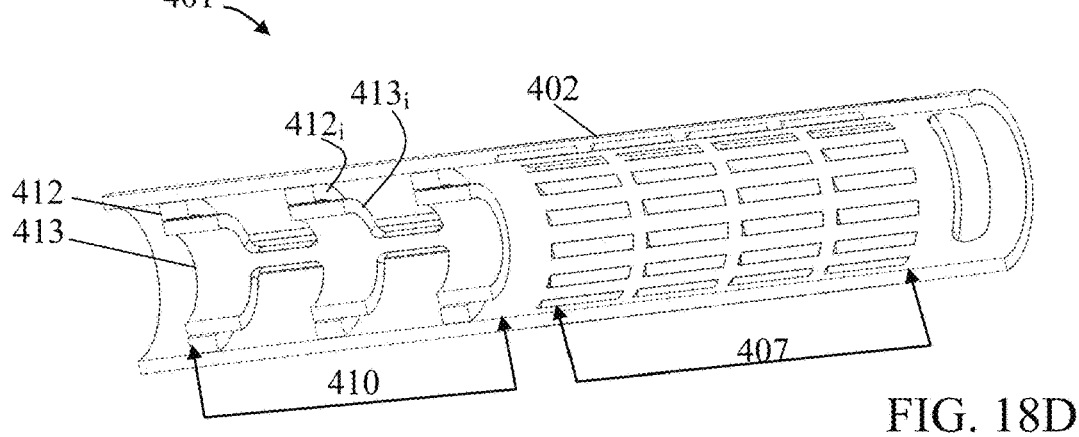

FIGS. 17A-17B illustrate a full isometric view and a sectional isometric view, respectively, of an exemplary embodiment of a distal portion of a catheter 370, which is optionally similar or even identical in design or/and configuration to catheter 100 or/and to catheter 120, and is optionally in a form of an embolization microcatheter. Optionally, catheter head 370 is a variation of catheter head 330 of FIG. 14, differentiated with that tubular wall 371 thereof it is made of polymeric tube 372 reinforced with a metal/spring coil 373, and is optionally applicable for manufacturing as a complete catheter rather than a catheter head connectable to a flexible tube.

Similar to catheter head 330, catheter 370 includes a proximal outlet 374 which is configured to allow passage therethrough of the suspension fluid and to block passage therethrough of the particles. Proximal outlet 374 includes a plurality of staggered lines of circumferential slits 375 extending with a length thereof substantially vertically to a longitudinal axis of the catheter. Each slit 375 includes a gap having a width smaller than a minimal diameter of the prescribed particles (e.g., 40 microns or more, in diameter), thereby facilitating particles blocking. Furthermore, catheter 370 includes a flow restraining mechanism 376 configured as inwardly radial projections 377 in form of opened or/and closed rings. Flow restraining mechanism 376 is configured to dissipate kinetic energy thereby to decrease horizontal velocity component of the particles along a longitudinal axis of catheter head 370. In some embodiments, impregnation of polymeric tube 372 with coil 373 is set to have slits 375 in between rounds of the coil, such that coil 373 does not cover, fully or partially, any or most of the slits.

FIGS. 18A-18D illustrate an isometric view of a catheter head 401 (FIG. 18A), a sectional isometric view of the catheter head 401 (FIG. 18B), a cross-sectional isometric view of the catheter head 401 (FIG. 18C), and a sectional orthogonal view of the catheter head 401 (FIG. 12D). Catheter head 401 is optionally part of a catheter similar or even identical in design or/and configuration to catheter 100 or/and to catheter 120, and is optionally in a form of an embolization microcatheter.

Catheter head 401 includes a tubular head wall 402 which includes a proximal head end 403 and a distal head end 404. Tubular head wall 402 encloses a head lumen 405 extending along head wall 402 and opened to a distal outlet 406 at distal head end 404 and is opened also to a proximal outlet 407 proximally to distal outlet 406. Catheter head 401 is connectable to a flexible tube with proximal head end 403, using connecting cavities 408, for integrating into a catheter (such as catheter 100). Connection is optionally done by melting distal portion of the of the flexible tube and allowing re-hardening over connecting cavities 408, or/and using adhesive.

Distal outlet 406 is shaped or/and sized to allow passage therethrough of the suspension fluid and the particles, and proximal outlet 407 is configured to allow passage therethrough of the suspension fluid and to block passage therethrough of the particles. Proximal outlet 407 includes a plurality of tangential longitudinal slits 409 extending with a length thereof substantially parallel to a longitudinal axis X of the catheter around and along a section of catheter head 401. Each slit 409 is not opened to head lumen 405 through a substantially inwardly-radial (straight) path but rather through a non-radial path curved substantially counterclockwise (or, alternatively, clockwise), substantially tangent to periphery of head wall 402. Each slit 409 includes a gap having a width smaller than a minimal diameter of the prescribed particles (e.g., 40 microns or more, in diameter), thereby facilitating particles blocking.

Catheter head 401 includes a flow restraining mechanism 410 located in proximity to distal outlet 406, distally to proximal outlet 407, and is configured to modify flow of the suspension, so as to decrease horizontal velocity component of the suspended particles along longitudinal axis of the catheter head 401. Flow restraining mechanism 410 includes at least one inwardly radial projection provided as a plurality of longitudinally spaced concave orifices 411, originating from inner boundary of catheter head lumen 405, projected substantially inwardly and radially, and then bent substantially in a proximal direction towards proximal outlet 407.

Each concave orifice 411 is configured to resist suspension flowing thereacross for resisting (choking) the suspension portion that is pressurized to pass distally therethrough under a pressure that is developed in catheter head lumen 405 during injection. The plurality of concave orifices 411 contributes to a positive pressure difference between lumen pressure and surrounding (blood vessel) pressure. As a result, and also due to a certain ratio between total opened cross section of proximal outlet 407 and (total) opened cross section of distal outlet 406, the velocity of the suspension fluid volume dispersed through proximal outlet 407 is substantially greater than horizontal velocity component of the suspended particles (with remaining suspension fluid) along longitudinal axis at the exit of distal outlet 406.

In this exemplary embodiments, flow restraining mechanism 410 is formed as an insert assembly, connected in head lumen 405, which includes an outer tubular chain of orifices 412 concentrically connected to an inner tubular chain of orifices 413, forming (in this example) three pairs of ring-like orifices. In each pair ("i"), an inner ring 413$_i$ extends to a greater length in a proximal direction relative to a corresponding outer ring 412$_i$ thereby forming a single concave orifice.

In some embodiments, outer diameter tubular head wall 402 is equal to or less than about 4 mm, optionally equal to or less than about 1 mm, or/and is configured for insertion into a small blood vessel originating from a celiac or hepatic artery.

In some embodiments, head wall 402 is made of a metallic material. In some such embodiments, the slits 409 are formed by one of laser cutting, laser drilling, etching, EDM, or any combination thereof. In some other embodiments, head wall 402 is made of a polymeric material, and in some such embodiments, the slits 409 are formed by one of femtolaser and skiving.

FIGS. 19A-19B illustrate a full isometric view and a sectional isometric view, respectively, of an exemplary embodiment of a catheter head 420, which is optionally similar or even identical in design or/and configuration to catheter 100 or/and to catheter 120, and is optionally in a form of an embolization microcatheter. Optionally, catheter head 420 is a variation of catheter head 330 of FIG. 14, differentiated with that a flow restraining mechanism 421 thereof incorporates an oblique helix 422 which includes a number of adjacent ring-like elements 422$_i$, each ring-like element has a bore being slightly further off-centered than a proximally-adjacent ring-like element, relative to a longitudinal axis X of catheter head 420. Flow restraining mechanism 421 is configured to dissipate kinetic energy thereby to decrease horizontal velocity component of the particles along longitudinal axis X.

Similar to catheter head 330, catheter head 420 includes a proximal outlet 423 which is configured to allow passage therethrough of the suspension fluid and to block passage therethrough of the particles. Proximal outlet 423 includes a plurality of staggered lines of circumferential slits 424 extending with a length thereof substantially vertically to a longitudinal axis of the catheter. Each slit 424 includes a gap having a width smaller than a minimal diameter of the prescribed particles (e.g., 40 microns or more, in diameter), thereby facilitating particles blocking.

Another variation for catheter 100 or/and catheter 120, or any of the previously shown catheters/catheter heads, is shown FIGS. 20A-20B which illustrate a full isometric view and a sectional isometric view, respectively, of a catheter head 430 including a first (proximal) section 431 of circumferential slits 432 and a second (intermediate) section 433 of pores 434. A plurality of inwardly radial projections 435 (ring-like shaped), configured together as a flow restraining mechanism, are distributed along catheter head length between first section 431 and a distal outlet 436 of catheter head.

Additional exemplary illustrative description of implementing exemplary embodiments of the invention follows.

Any of the herein disclosed catheters (microcatheters), and exemplary embodiments thereof, may be used for practicing and performing any of the herein disclosed methods, and exemplary embodiments thereof, and vice versa. In a non-limiting manner, for example, hereinabove illustratively described exemplary catheters 100, 120, 140, 160, 30, 50, 60, 70, 200, 320, and 370, may be used for practicing and performing herein disclosed method for modifying and delivering a suspension into a blood vessel of a subject, and, may also be used for practicing and performing herein disclosed method for performing local embolization in a small blood vessel feeding a cancerous target bodily part of a subject.

For example, with reference to FIGS. 1A-1B, the method for modifying and delivering a suspension into a blood vessel of a subject, the suspension being a mixture of particles suspended in a suspension fluid, includes the following exemplary steps (procedures). Providing catheter 100 having proximal inlet 113, distal outlet 107, and proximal outlet 108 located between proximal inlet 113 and distal outlet 107. Positioning distal outlet 107 adjacent a target location in blood vessel BV. Injecting into proximal inlet 113 a premade suspension 111 of the particles suspended in a total volume of the suspension fluid. Allowing excess volume 102 of the suspension fluid with the suspended particles to disperse via proximal outlet 108. Delivering into blood vessel BV, via distal outlet 107, a remaining volume 112 of the suspension fluid with the suspended particles.

In exemplary embodiments, the step (procedure) of allowing includes filtering premade suspension 111. In exemplary embodiments, such filtering includes blocking passage of the suspended particles through proximal opening 108. In exemplary embodiments, the method includes reducing a velocity (v) of the suspension fluid between proximal inlet 113 and distal outlet 107 by half or less. In exemplary embodiments, the method includes reducing a velocity (v) of the suspension fluid between proximal outlet 108 and distal outlet 107 by half or less. In exemplary embodiments, the method includes reducing a momentum (m·v) of the suspension fluid between proximal inlet 113 and distal outlet 107 by ninth or less. In exemplary embodiments, the method includes reducing a momentum (m·v) of the suspension fluid between proximal outlet 108 and distal outlet 107 by eighth or less. In exemplary embodiments, the method includes reducing a mass (m) of the suspension fluid between proximal outlet 108 and distal outlet 107 by half or less. In exemplary embodiments, the method includes reducing a flow rate of the suspension fluid between proximal outlet 108 and distal outlet 107 by fourth or less. In exemplary embodiments, the volumetric ratio between the total volume and the remaining volume 112 is at least four. In exemplary embodiments, the step (procedure) of delivering of the remaining volume 112 of the suspension fluid has a velocity of 20 cm/second or less.

Additionally, for example, with reference to FIGS. 1A-1B, the method for performing local embolization in a small blood vessel feeding a cancerous target bodily part of a subject, includes the following exemplary steps (procedures). Providing an embolization microcatheter 100 having distal outlet 107, proximal inlet 113, and proximal outlet 108 located between proximal inlet 113 and distal outlet 107. Positioning distal outlet 107 in small blood vessel BV upstream to the cancerous target bodily part. Injecting into proximal inlet 113 a premade suspension 111 of particles suspended in a suspension fluid. Allowing excess volume 102 of the suspension fluid with the suspended particles to disperse via proximal outlet 108 and blocking the particles from passing through proximal outlet 108. Delivering into small blood vessel BV a remaining volume 112 of the suspension fluid with the suspended particles, at least until creating an embolus sized for effective blocking of blood flow between distal outlet 107 and the cancerous target bodily part. In exemplary embodiments, the suspension fluid includes a contrast enhancing agent.

Empirical Lab Results: Performance of an Exemplary Catheter as Disclosed Herein Compared to That of an Exemplary Commercial Catheter FIG. 21A-21D are schematic drawings based on and representing orthogonal view frames of video-recording comparing: (I) lab test results of an exemplary catheter 600 (in accordance with some embodiments of the invention), with (II) lab test results of a commercial catheter 700 (in accordance with prior art disclosure), using a lab-test setup 500. Lab tests were performed on Jan. 24, 2016.

Setup 500 included a bifurcation 501, a first branch 502 configured for simulating a target blood vessel feeding a target bodily part, and a second branch 503 configured for simulating a (non-target) branching blood vessel to the small blood vessel. Setup 500 was set to continuously stream a blood simulant through bifurcation 501, first branch 502 and second branch 503 with similar properties and flow characteristic as in the simulated cardiovascular system. Setup 500 parts and blood simulant were transparent and allowed direct visualization of each of the catheters and any colored (fluorescence) substance injected therein. The blood simulant was injected (using a pump) with pulsatile pressure of 80-120 mm Hg, such that each of first branch 502 and second branch 503 received a flow rate of 4 ml/min.

A suspension of beads 505 in a suspension fluid 506 was prepared. Beads 505 specifications were: about 100 microns size, colored fluorescent microspheres, by 'Cospheric LLC' (Santa-Barbara, Calif., USA). Suspension was injected in both cases using a syringe pump, model "Fusion™ 720", by Chemyx Inc. (Stafford, Tex., USA).

Exemplary catheter 600 included a single infusion lumen opened to a distal outlet 601 and a proximal outlet 602. Distal outlet 601 delivered suspension fluid 506 and beads 505, whereas proximal outlet 602 included a plurality of side openings in form of slits sized to deliver suspension fluid 506 and to block passage therethrough of beads 505. Smallest cross sectional dimension (width/gap) of each slit was about 25 microns. Proximal outlet 602 included a combination of longitudinal slits and circumferential slits, same as in proximal outlet 355 of FIG. 15. Flow restraining mechanism included three consecutive, spaced, (ring-like) orifices, each having a bore of about 0.4 mm.

Commercial catheter 700 used was 2.7 Fr (0.9 mm) sized, model "Progreat"™, by Terumo Medical Corporation (Somerset, N.J., USA), and included a single infusion lumen (inner diameter 0.065 mm) opened to a distal outlet 701 (but not to any proximal outlet) sized to deliver suspension fluid 506 and beads 505.

Figure 21A:
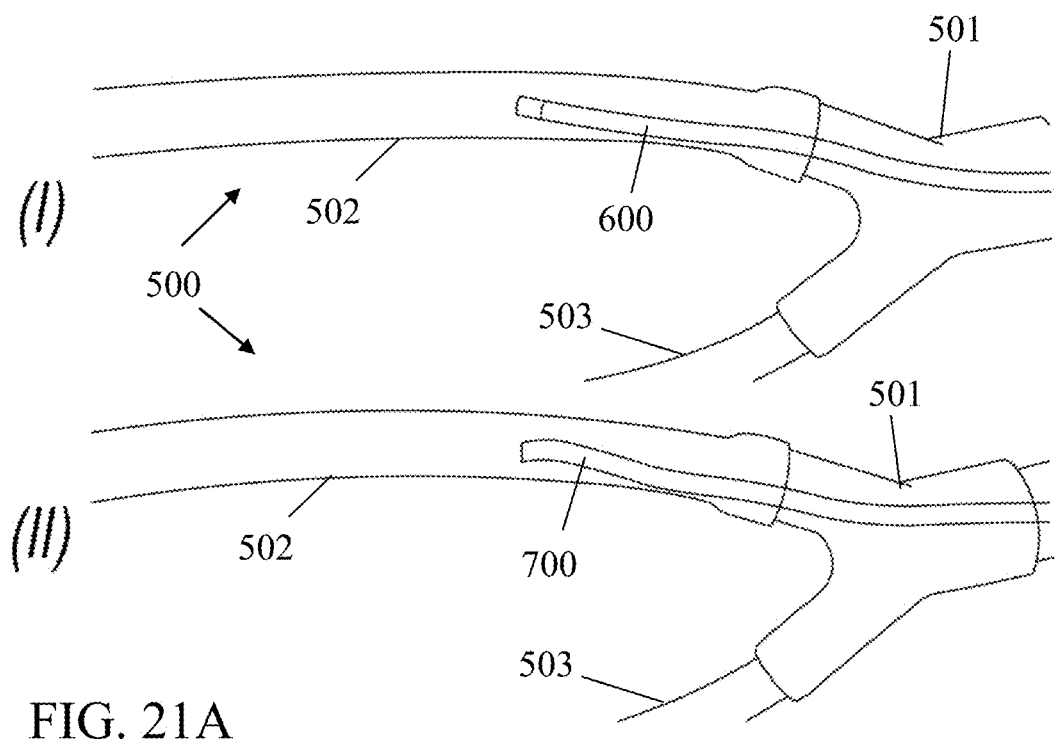
FIGS. 21A-21D are schematic drawings based on and representing orthogonal view frames of exemplary video frames comparing exemplary comparative lab test results obtained using an exemplary embolization microcatheter (according to some embodiments of the invention) verses an exemplary commercially available embolization microcatheter.
Figure 21B:
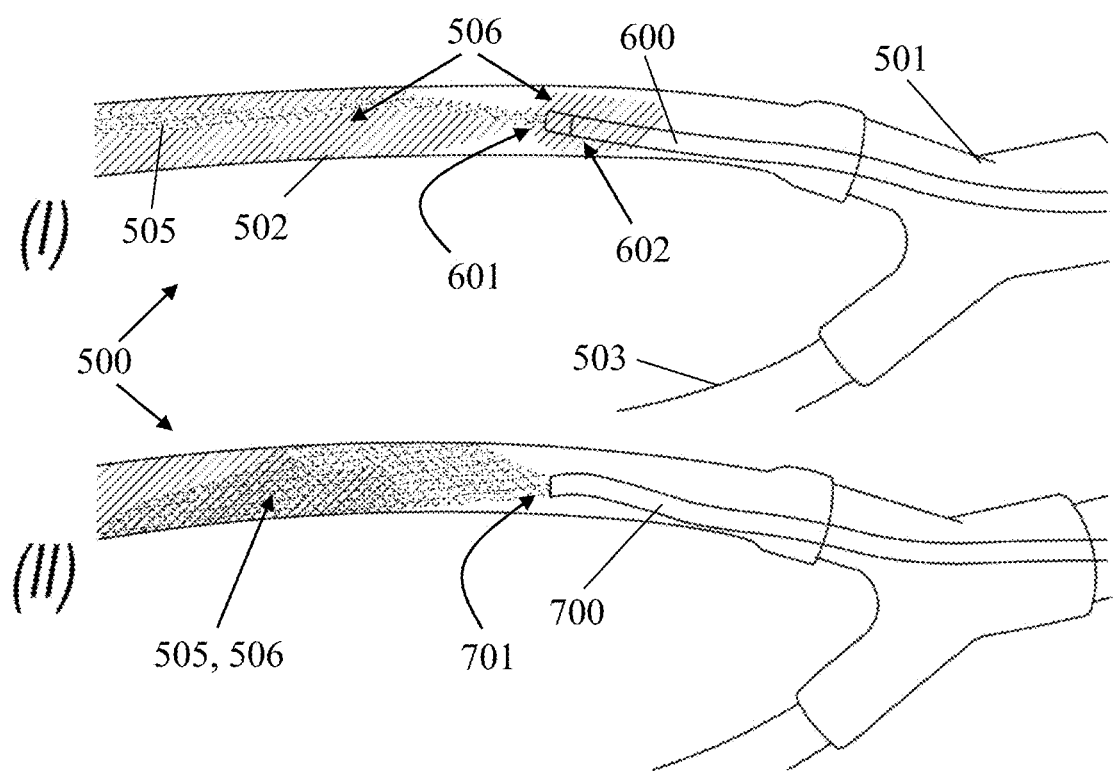
Figure 21C:
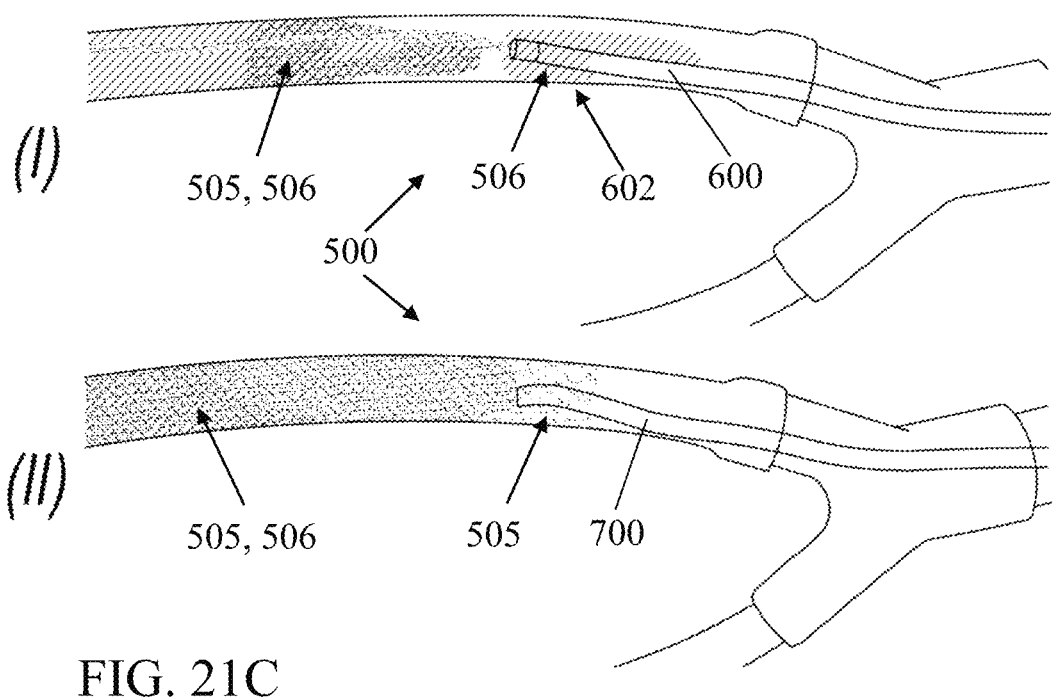
Figure 21D:
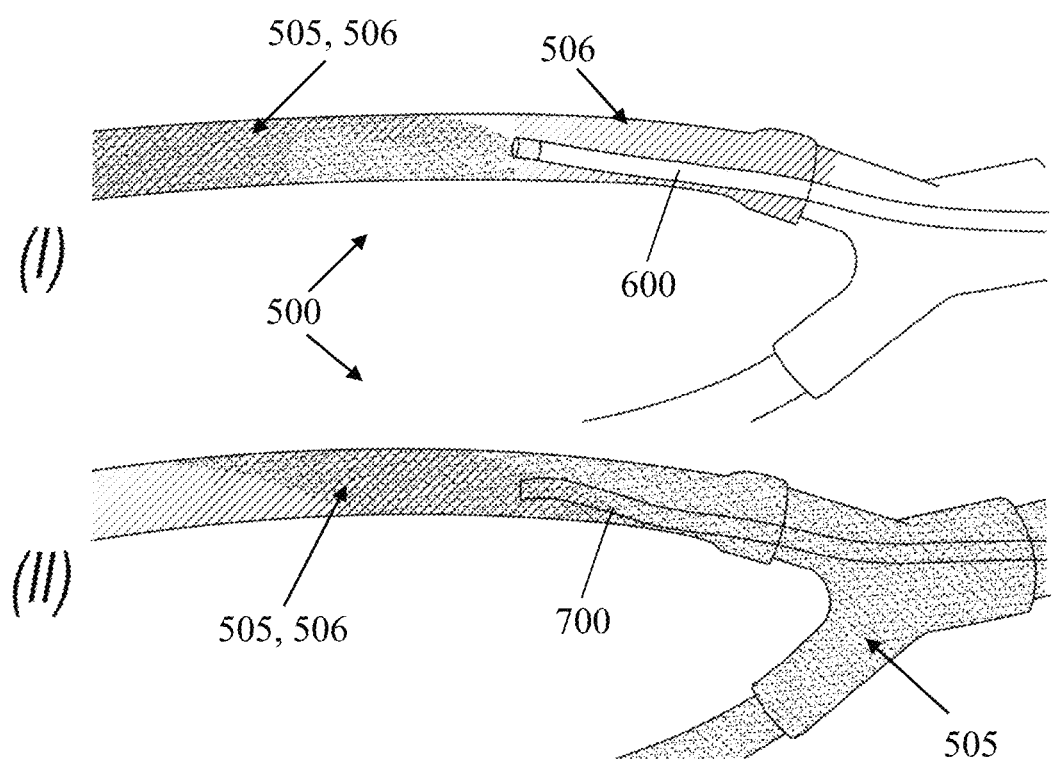

In FIG. 21A, (I) and (II) show catheters 600 and 700, respectively, positioned in setup 500 before infusions of suspension. In FIG. 21B, (I) and (II) show catheters 600 and 700, respectively, at the beginning of suspension infusion, before emergence of beads reflux. In FIG. 21C, (I) and (II) show catheters 600 and 700, respectively, at a preliminary stage of beads reflux. In FIG. 21D, (I) and (II) show catheters 600 and 700, respectively, at an advance stage of beads reflux.

As demonstrated, in FIG. 21D, (I) shows that dispersion of suspension fluid 506 via proximal outlet (slits) 602 of exemplary catheter 600 prevented any visible reflux of beads 505 toward bifurcation 501. By strong contrast, in FIG. 21D, (II) shows that commercial catheter 700 allowed for substantial beads reflux that passed bifurcation 501 and even entered into second branch 503.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'. The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', ' from 2 to 4', ' from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range. Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An embolization microcatheter for modifying and delivering a suspension to a subject, the suspension includes particles suspended in a suspension fluid, the microcatheter comprising:
   a tubular wall comprising a proximal wall end, a distal wall end, and a lumen extending between said wall ends and configured to allow passage therethrough of the suspension;
   a distal outlet at the distal wall end; and
   a plurality of side openings formed in the tubular wall proximally to the distal outlet,
   wherein the distal outlet is shaped and/or sized to allow passage therethrough of both the suspension fluid and the particles,
   wherein the plurality of side openings is in the form of longitudinal slits having a longer length and a shorter length, wherein the longer length is parallel to a longitudinal axis extending from a proximal end to a distal end of the embolization microcatheter, the plurality of side openings for blocking passage therethrough of the particles,
   wherein the plurality of side openings is distributed around and/or along a section of the tubular wall,
   wherein the longitudinal slits have a smallest cross sectional dimension equal to or less than about 100 microns and wherein a total opened cross section of the longitudinal slits is at least about 0.5 mm$^2$, such that a ratio of a momentum of the suspension flowing proximally to the longitudinal slits and a momentum of the suspension flowing distally to the longitudinal slits is at least 3,
   wherein the embolization microcatheter has a length suitable for performing embolization procedures, and
   wherein the microcatheter is configured to prevent back flow during continuous delivery of the particles through the distal outlet.

2. The embolization microcatheter according to claim 1, wherein said plurality of side openings is distributed around and/or along a section of said tubular wall, wherein said plurality of side openings has a smallest cross sectional dimension equal to or less than about 30 microns.

3. The embolization microcatheter according to claim 1, wherein the particles configured to be delivered include a solid embolic material and/or a particulate embolic agent.

4. The embolization microcatheter according to claim 1, wherein the longitudinal slits have a width less than a minimal diameter of the particles, so as to facilitate said passage blocking.

5. The embolization microcatheter according to claim 1, comprising a length limiting rod-like element extending parallel to the longitudinal axis of said microcatheter across said plurality of side openings, so as to resist and/or prevent elongation of the microcatheter about said plurality of side openings.

6. The embolization microcatheter according to claim 5, wherein said rod-like element includes lateral extensions in a form of closed and/or opened rings curved in conformity to inner boundaries of said lumen.

7. The embolization microcatheter according to claim 1, comprising a flow restraining mechanism located in proximity to said distal outlet, and configured to decrease a horizontal velocity component of the particles along the longitudinal axis of the embolization microcatheter.

8. The embolization microcatheter according to claim 7, wherein said flow restraining mechanism comprises a helix positioned in the lumen of the embolization microcatheter, adjacent said distal outlet, and; shaped and dimensioned so as to increase a lateral velocity component of the particles and to decrease a longitudinal velocity component of the particles.

9. The embolization microcatheter according to claim 7, wherein said flow restraining mechanism comprises at least one inwardly radial projection originating from an inner boundary of said lumen, configured to resist the suspension flowing thereacross; and wherein said at least one inwardly radial projection includes a plurality of longitudinally spaced opened and/or closed ring elements.

10. The embolization microcatheter according to claim 1, wherein an outer diameter of said tubular wall is equal to or less than about 4 mm.

* * * * *